Figure 1:
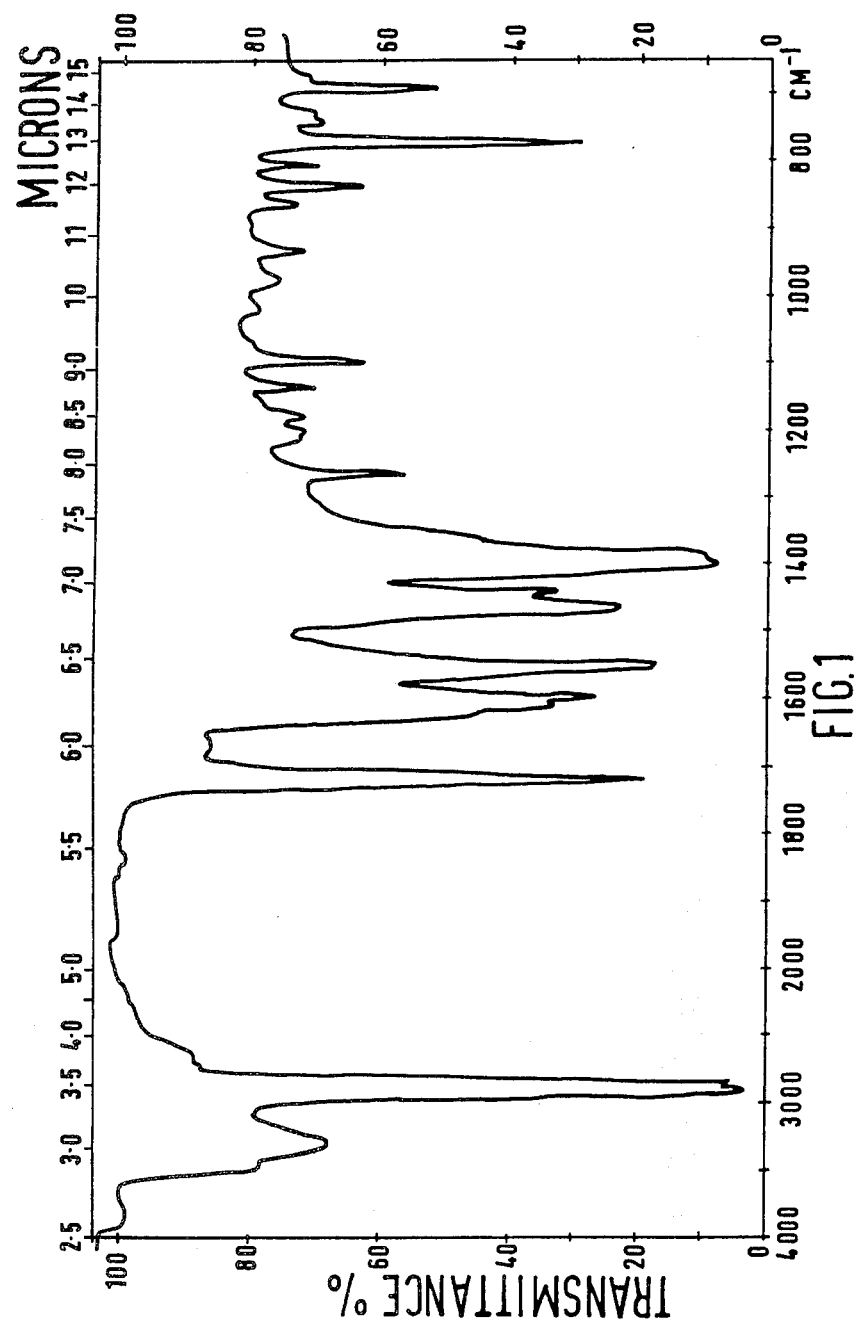

United States Patent [19]
Hodson et al.

[11] 3,939,276
[45] Feb. 17, 1976

[54] CYCLIC CARBONYL COMPOUNDS

[75] Inventors: Harold Francis Hodson, Hayes; John Frederick Batchelor, Beckenham, both of England

[73] Assignee: Burroughs Wellcome Co., Research Triangle Park, N.C.

[22] Filed: Mar. 6, 1973

[21] Appl. No.: 338,415

Related U.S. Application Data

[63] Continuation-in-part of Ser. No. 287,042, Sept. 7, 1972.

[52] U.S. Cl. ............... 424/317; 424/248; 424/250
[51] Int. Cl.² ..................................... A61K 31/19
[58] Field of Search ................ 424/317, 248, 250

[56] References Cited
UNITED STATES PATENTS

| | | | |
|---|---|---|---|
| 3,642,997 | 2/1972 | Shen et al. | 424/317 |
| 3,706,768 | 12/1972 | Bays | 424/269 |

FOREIGN PATENTS OR APPLICATIONS

| | | |
|---|---|---|
| 770,937 | 8/1971 | Belgium |

OTHER PUBLICATIONS

Physicians Desk Reference, (PDR), 1971, pp. 926–936.
Stedman's Medical Dictionary 21st Edition, 1966, pp. 52, 105, 791–792.

*Primary Examiner*—Norman A. Drezin
*Attorney, Agent, or Firm*—Donald Brown

[57] ABSTRACT

Certain fluorenone and anthraquinone compounds, each of which is 2-substituted by a carboxyl group or a salt, ester or optionally substituted amide thereof and each of which is optionally substituted in the 5,6-,7- or 8- position, by a second carboxyl group, salt, ester or optionally substituted amide thereof, the substitutent in the 5,6-7- or 8- position of the fluorenone compounds, also being selected from cyano, halogen, nitro, alkyl, alkoxy and acyl, are useful for the relief or prophylaxis of allergic conditions.

11 Claims, 11 Drawing Figures

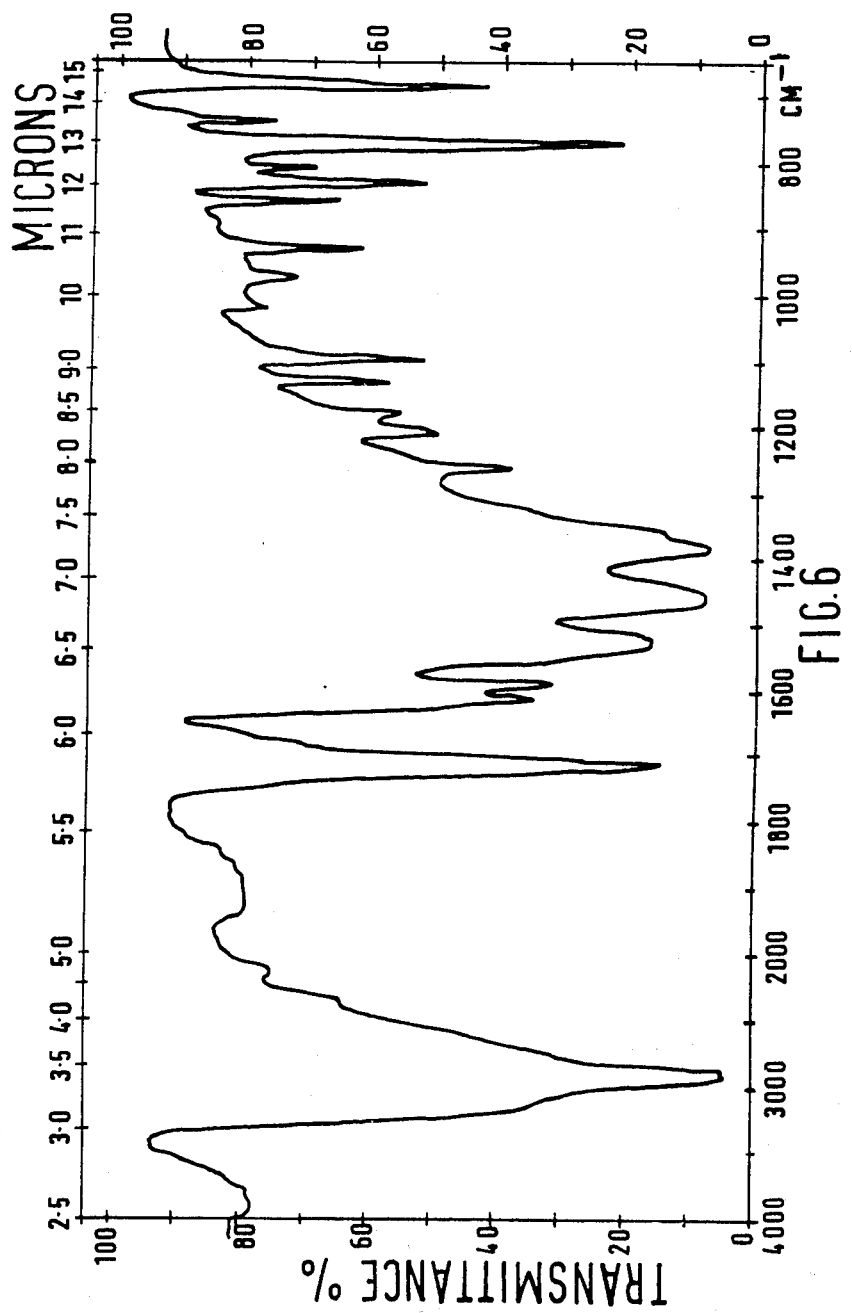

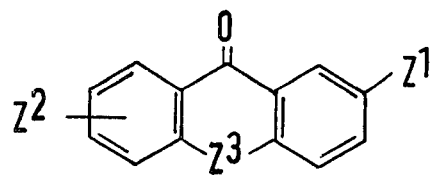
I
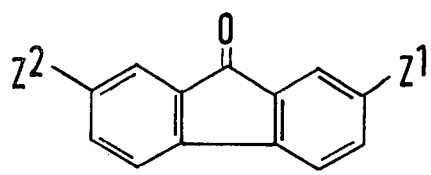
II
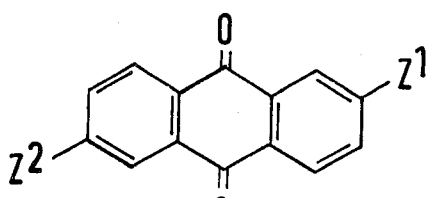
III
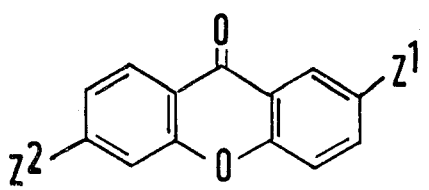
IV
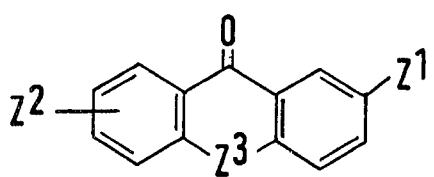
V
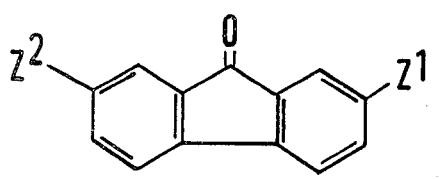
VI

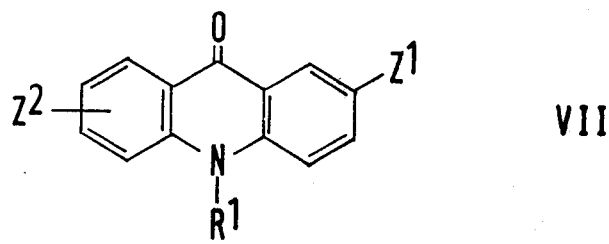 VII
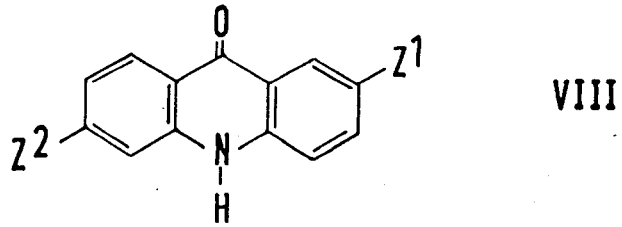 VIII
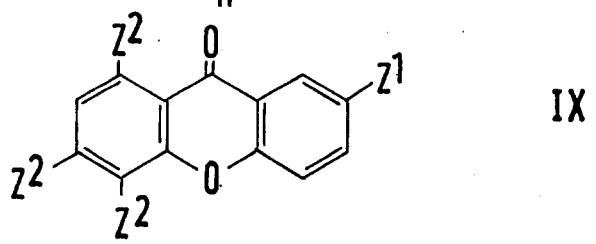 IX
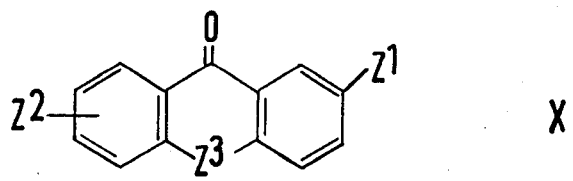 X
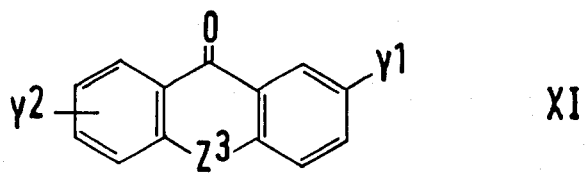 XI
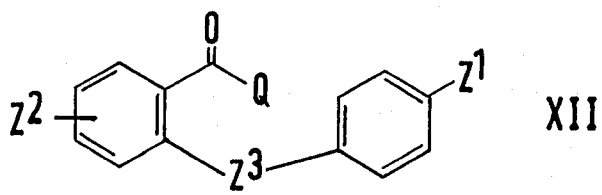 XII

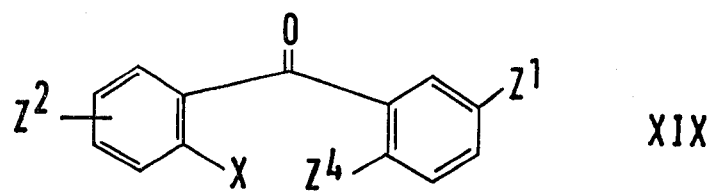
XIX
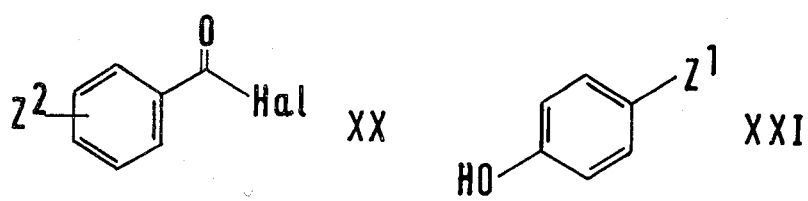
XX   XXI
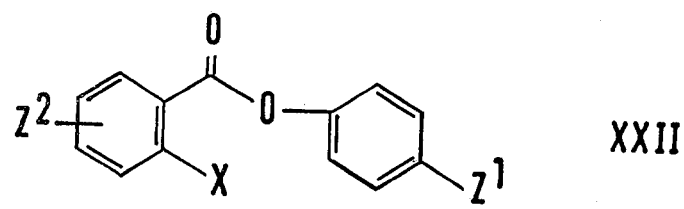
XXII
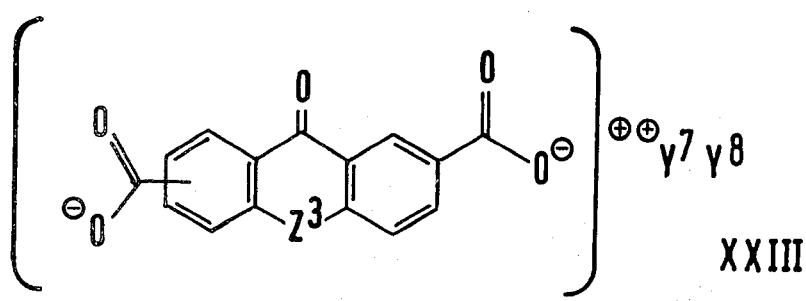
XXIII
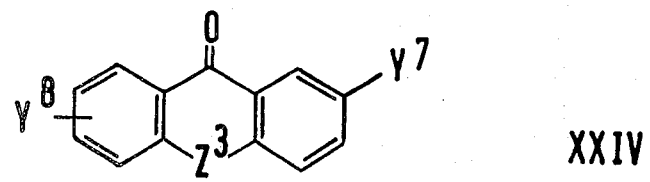
XXIV

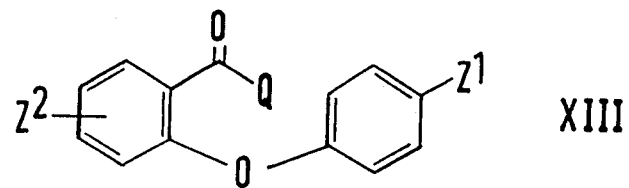 XIII
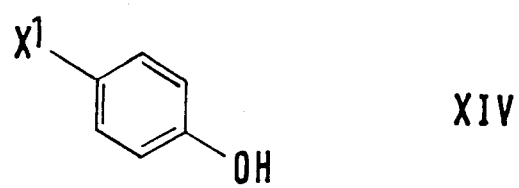 XIV
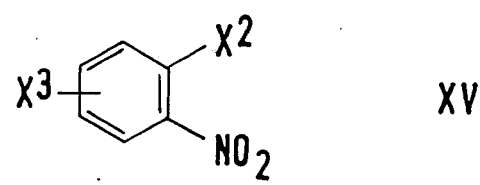 XV
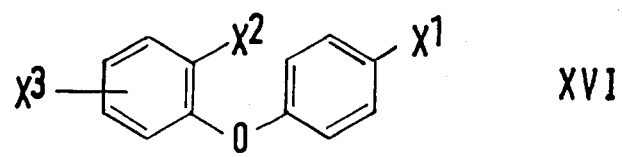 XVI
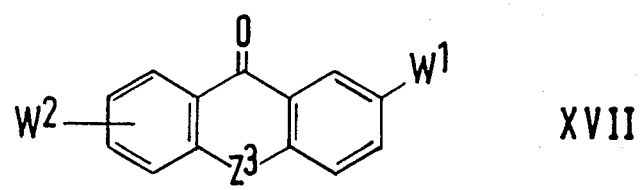 XVII
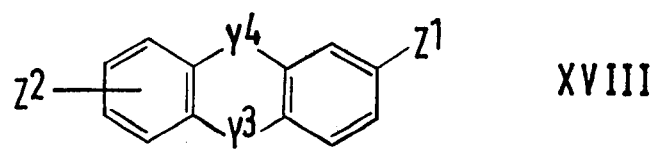 XVIII

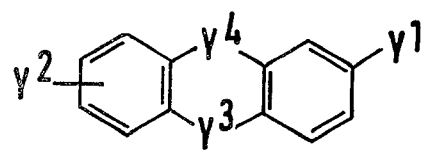
XXV
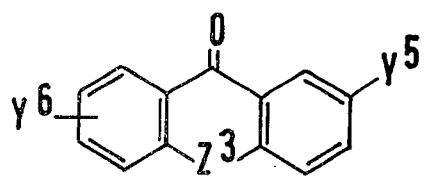
XXVI
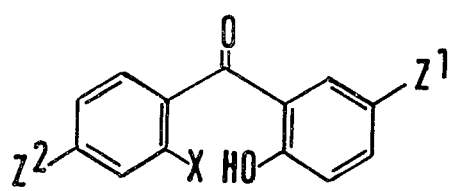
XXVII
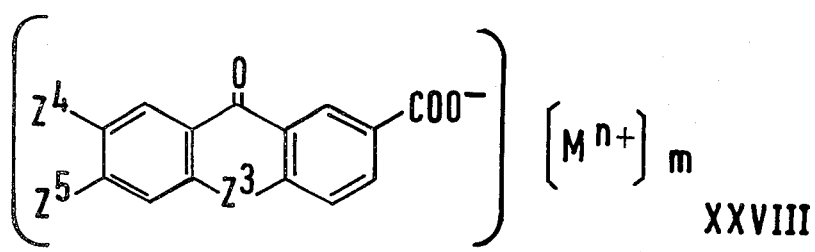
XXVIII
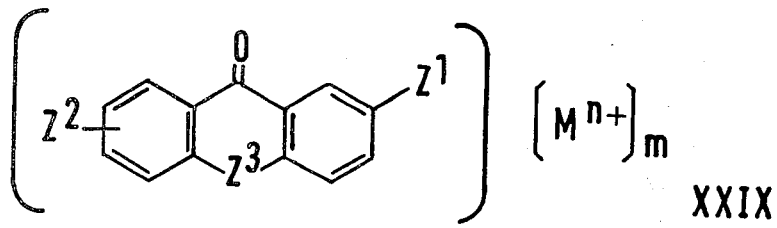
XXIX
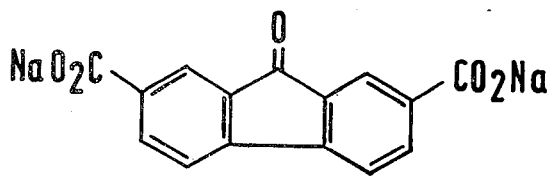
XXX

CYCLIC CARBONYL COMPOUNDS

This application is a continuation-in-part of U.S. patent application Ser. No. 287,042 filed Sept. 7, 1972, now pending.

The invention relates to tricyclic compounds having medicinal properties, the synthesis of the compounds and their adaptation for medicinal use.

It has been found that tricyclic compounds of formula I defined hereinbelow are active in mammals and in in vitro mammalian preparations as inhibitors of allergic reactions associated with reaginic antibodies of the kind responsible for asthma in man, and that this effect is attributable to the suppression of the release of anaphylactic mediators.

In formula I

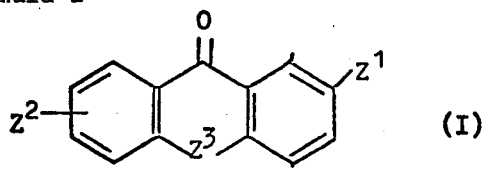

$Z^1$ is a carboxyl group, a carboxylate salt group, an alkyl carboxylate group wherein the alkyl moiety has 1 to 6, preferably 1 to 4 carbon atoms or a carboxamide group optionally N-substituted by alkyl having 1 to 6, preferably 1 to 4 carbon atoms; $Z^3$ represents a bond or is a carbonyl group; and $Z^2$ is a substituent and has the same meaning as $Z^1$ or is a hydrogen atom or when $Z^3$ is a bond, $Z^2$ is a nitro group, a cyano group, a halogen atom preferably chlorine or bromine, an acyl group, an alkyl group or an alkoxy group wherein the "alkyl" moiety of each of the acyl, alkyl and alkoxy groups has 1 to 6 carbon atoms.

Especially active compounds of formula I are fluorenone-2, 7-dicarboxylic acid and pharmaceutically acceptable salts thereof, especially Disodium fluorenone-2,7-dicarboxylate of formula

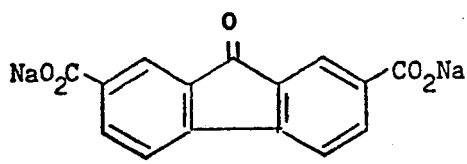

as well as the dipotassium and diammonium salts of Fluorenone-2,7-dicarboxylic acid.

Highly active compounds of formula I are Anthraquinone-2,6-dicarboxylic acid and pharmaceutically acceptable salts thereof, especially the disodium, dipotassium and diammonium salts thereof.

Substantially active compounds of formula I include:

7-Methoxyfluorenone-2-carboxylic acid;
7-Cyanofluorenone-2-carboxylic acid;
7-Ethylfluorenone-2-carboxylic acid; and pharmaceutically acceptable salts thereof.

Other moderately active compounds of formula I include:

7-Chlorofluorenone-2-carboxylic acid;
7-Acetylfluorenone-2-carboxylic acid;
7-Carboxamidofluorenone-2-carboxylic acid;
7-Nitrofluorenone-2-carboxylic acid;
Fluorenone-2-carboxylic acid;
Anthraquinone-2-carboxylic acid; and pharmaceutically acceptable sals thereof.

The inhibition activity of the compounds of formula I has been demonstrated (a) in tests using the response of passive cutaneous anaphylaxis (PCA test) in which is measured the skin reaction produced as the result of interaction between specific antigen injected intravenously and cell-fixed reaginic antibody previously injected into the skin of a mammal (see for example Z. Ovary: Fedn. Proc. Am. Soc. exp. Biol. 24, 94 (1965)), (b) by measurement of the amount of histamine released after antigen challenge of peritoneal mast cells from actively sensitised rats (see for example, 1. Acta Pharmacol. et Toxicol. 30, supp. 1 (1971), 2. Thorax, 27/1, 38 (1972), and (c), by measurement of the histamine released from human chopped lung tissue passively sensitised in vitro with reaginic antibody when challenged with the homologous antigen (Br. Med. J. 3,272 (1968)). The activity of acids of formula I has been demonstrated as described hereinabove using solutions of the carboxylate anion.

For the sake of convenience, compounds of formula I wherein either of $Z^1$ and $Z^2$ is or both are an alkyl carboxylate group, shall hereinafter be referred to as 'esters' of formula I. Similarly references to 'amides' of formula I shall be construed as references to compounds of formula I wherein one or both of $Z^1$ and $Z^2$ is an optionally substituted carboxamide, and references to 'salts' of formula I shall mean compounds of formula I wherein one or both of $Z^1$ and $Z^2$ is a carboxylate salt group.

Pharmaceutically acceptable salts of formula I include ammonium salts, alkali metal salts such as sodium and potassium salts, alkaline earth salts such as magnesium and calcium salts, and salts of organic bases, for example, amine salts such as triethanolamine and diethylaminoethylamine salts, and piperazine and morpholine salts. Especially valuable are water soluble salts of formula I most perferably those having a solubility in water of at least 1 mg/ml.

The anti-allergic activity of the salts of formula I lies in the anion and the nature of the cation does not contribute to the activity, but for medicinal purposes the cation must of course be pharmaceutically acceptable.

Suitable substituted carboxamide groups include N-alkyl and N,N-dialkyl substituted carboxamide groups wherein the alkyl moiety is an alkyl group having 1 to 6 carbon atoms, preferably 1 to 4 carbon atoms.

Fluorenone compounds of the present invention include tricyclic compounds of formula

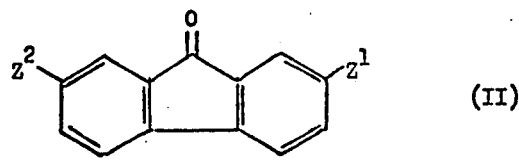

wherein $Z^1$ and $Z^2$ are the same or different and each is selected from a carboxyl group, a carboxylate salt group, an alkyl carboxylate group, having 1 to 6 carbon atoms in the alkyl moiety, and a carboxamide group optionally N-substituted by an alkyl group having 1 to 6 carbon atoms.

Anthraquinone compounds of the present invention include tricyclic compounds of formula

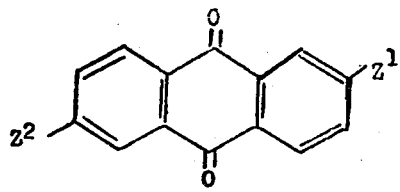

(III)

wherein $Z^1$ and $Z^2$ are the same or different and each is selected from a carboxyl group, a carboxylate salt group, an alkyl carboxylate group having 1 to 6 carbon atoms, and a carboxamide group optionally N-substituted by an alkyl group having 1 to 6 carbon atoms.

Novel fluorenone compounds of the present invention include tricyclic compounds of the formula

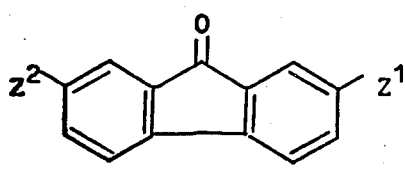

(VI)

wherein $Z^1$ is a carboxyl group or a carboxylate salt group and $Z^2$ is a halogen atom, a cyano group, an alkyl group having 2 to 4 carbon atoms or a carboxamide group optionally N-substituted by alkyl having 1 to 6 carbon atoms.

Novel compounds of the present invention also include solid tricyclic compounds of formula

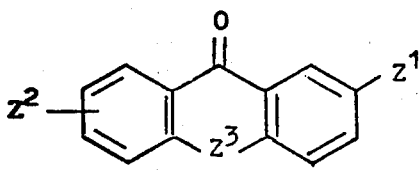

(X)

wherein $Z^2$ is a carboxylate salt group, $Z^3$ represents a bond or is a carbonyl group, $Z^2$ is selected from a cyano group, a halogen atom, a nitro group, an alkyl group, an acyl group or an alkoxy group wherein the 'alkyl' moiety of the alkyl, acyl and alkoxy groups is an alkyl group having 1 to 6 carbon atoms.

The present invention also provides as novel products solid disodium fluorenone-2,7-dicarboxylate, disodium fluorenone-2,7-dicarboxylate monohydrate and particles of disodium fluorenone-2,7-dicarboxylate having a diameter of from 0.5 to $7\mu$.

Preparation of compounds of formula I may be effected by any method known in the art of preparing them and compounds of analogous chemical structure. In general the compounds of formula I wherein one or both of $Z^1$ and $Z^2$ is a carboxylate derivative (for example an amide, ester or salt), are prepared by suitable treatment of the corresponding acid. However, in certain circumstances it is possible to prepare such derivatives without prior isolation of the carboxylic acid, either by the choice of suitable reactants or by forming the desired derivative in a reaction mixture of the acid, without first isolating the acid.

Methods for the preparation of dicarboxylate acids and salts of formula are described hereinbelow, but it will be understood that in some instances the methods may be adopted to yield the corresponding esters or amides of formula I 1. Hydrolysis of a compound of formula XI

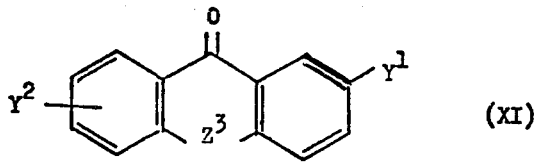

(XI)

wherein $Y^1$ is a carboxyl group precursor, such as a nitrile group, trichloromethyl group or a group $COL^1$ wherein $L^1$ is a leaving group, such as a nucleophilic atom or group, for example, a trichloromethyl group, an optionally substituted amino group, a halogen atom or an alkoxy group; $Y^2$ is a carboxyl group or a group $Y^1$ precursor as defined above; and $Z^3$ has the meaning defined in formula I. Hydrolysis is conveniently effected by heating a compound of formula XI with a dilute aqueous alkali, or with a dilute aqueous mineral acid optionally with an organic acid. For example, one may use dilute sulpuric acid, dilute hydrochloric acid with acetic acid, or dilute aqueous sodium hydroxide solution. Hydrolysis with aqueous alkali will yield inter alia an aqueous solution of a dicarboxylate salt but if it is desired to collect the maximum amount of dicarboxylic acid, then the reaction mixture should be acidified when hydrolysis is completed to precipitate the acid. On the other hand if the desired end-product is the dicarboxylate salt, then following hydrolysis, the cation of the desired salt may be added to precipitate the desired salt by the common ion effect without prior isolation of the corresponding acid.

By means of nucleophilic substitution reactions analogous to hydrolysis, for example, alcoholysis and ammonolysis, compounds of formula I other than the dicarboxylic acid may be prepared directly from compounds of formula XI. Thus reaction of a compound of formula XI with an appropriate alcohol yields an ester of formula I, and reaction with ammonia or an appropriate primary or secondary amine yields an amide of formula I. 2. Cyclisation of a compound of formula XII

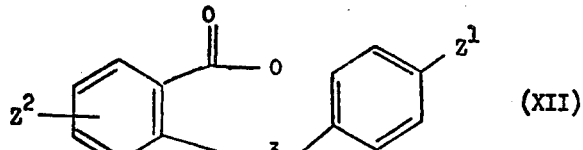

wherein $Z^1$, $Z^2$ and $Z^3$ have the meaning defined in formula I and Q is a hydroxyl, alkoxy or an optionally substituted amino group, a halogen atom, or a $RCO_2$ group, a $ROCO_2$ group or a $RSO_3$ group wherein R is alkyl or aryl. Cyclisation may be effected by heating a compound of formula XII at an elevated temperature, for example up to about 300°C. Preferably heating is carried out in the presence of a Lewis acid under anhydrous conditions or a protonic acid, optionally in the presence of a non-polar solvent. Preferred Lewis acids include boron trifluoride and aluminium trichloride and preferred protonic acids include sulphuric, hydrochloric and polyphosphoric acids. If, however, $Z^2$ is a carboxylate substituent in the 5-position of the nascent compound of formula I, reaction conditions and/or the group Q must be chosen so as to avoid reaction of the group $Z^2$.

In the case of anthraquinone compounds of formula I cyclisation to form the carbonyl linkage in the tricyclic nucleus may be effected to form either of the two carbonyl linkages of the tricyclic anthraquinone nucleus. 3. Oxidation of a compound of formula XVII

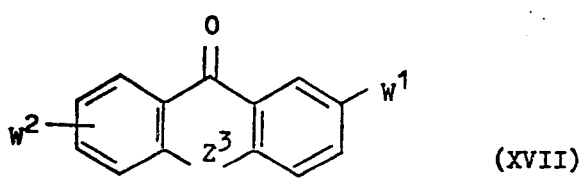

wherein $W^1$ and $W^2$ are each a lower alkyl group or a group $C(:O)R$ wherein R is an optionally substituted lower alkyl group having 1 to 4 carbon atoms, or is OH, provided that $W^1$ and $W^2$ are not both $C(:O)OH$ and $Z^3$ has the meaning defined in formula I. Oxidation of compounds wherein $W^1$ and/or $W^2$ are lower alkyl groups may be effected with such conventional oxidising agents as acid or alkaline aqueous potassium permanganate solution; chromium trioxide, for example, with acetic acid or sulphuric acid; oxygen in the presence of a conventional catalyst such as lead, cobalt and manganese salts, for example, lead acetates or aqueous solutions of sodium dichromate.

Oxidation of compounds wherein $W^1$ and/or $W^2$ are the groups $C(:O)R$ may be effected with such conventional oxidising agents as chromium trioxide, for example, with acetic acid or sulphuric acid; aqueous solutions of salts of hypochlorous and hypobromous acids in the presence of a base; sodium or potassium dichromate with acetic acid; or nitric acid. These oxidation procedures are advantageously effected with heating in the liquid phase. 4. Oxidation of a compound of formula XVIII

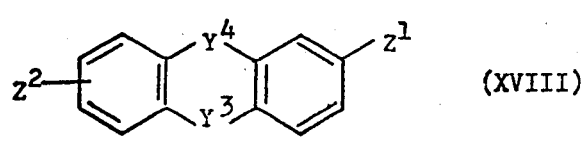

wherein $Z^1$ and $Z^2$ have the meaning defined hereinbefore in formula I, $Y^3$ is a group $Z^3$ as defined hereinbefore in formula I and $Y^4$ is a methylene group; or $Y^4$ and $Y^3$ are the same or different and are each selected from CH and CR wherein R is lower alkyl. Oxidation of compounds of formula XVIII may be effected with such conventional oxidising agents as nitric acid; aqueous solutions of hypochlorous and hypobromous acids in the presence of base; chromium trioxide, for example with acetic acid or with sulphuric acid; or aqueous solutions of sodium dichromate.

Oxidation of compounds of formula XVIII wherein $Y^4$ is a methylene group and $Y^3$ is a bond, or $Y^4$ and $Y^3$ are each CH, may also be effected with such conventional oxidising agents as oxygen in the presence of triton B in pyridine solution; or oxygen in the presence of potassium t-butoxide in the presence of t-butanol and dimethylsulphoxide.

Compounds analogous to the compounds of formula XVIII wherein either or both of $Z^1$ and $Z^2$ is replaced by a group $W^1$ or $W^2$ as defined in formula XVII, may also be oxidised so as to produce dicarboxylate acids or salts of formula I. Oxidation in the case of such compounds may be effected with such conventional oxidising agents as chromium trioxide, for example, with acetic acid or with sulphuric acid; or aqueous solutions of sodium dichromate. In the case of such compounds wherein neither of $W^1$ and $W^2$ is alkyl, oxidation may also be effected with such conventional oxidising agents as aqueous solutions of salts of hypobromous or hypochlorous acids in the presence of a base; or nitric acid. Advantageously any of the hereinbefore described oxidation procedures wherein aqueous solutions of sodium dichromate are employed, are carried out at an elevated temperature in a sealed container. Oxidation of the groups $W^1$ and $W^2$ in such a case is preferably effected at a temperature of from 200° to 210° C. Oxidation of the tricyclic anthracene; 9,10-dialkyl anthracene or anthrone nucleus in such a case is desirably effected at a temperature of from 250° to 260°C.

Pharmaceutically acceptable salts of acids of formula I are prepared by any conventional method, for example by neutralising the corresponding carboxylic acid with an appropriate Brønsted base, or by double decomposition of a salt of an acid of formula I so as to produce the desired salt of an appropriate pharmaceutically acceptable cation. The carboxylic acid may be either the isolated acid, or may be present in solution in the reaction mixture resulting from a preparation of the acid, for example by such a method as described hereinbefore. Suitable Brønsted bases include organic bases such as ethanolamine, and bases containing ammonium, and alkali metal and alkaline earth metal cations. Double decomposition may be effected advantageously in an ion exchange resin wherein a solution of a salt of an acid of formula I is passed through a cation exchange resin, the resin being charged with a pharmaceutically acceptable cation of the suitable base. Double decomposition may also be effected in ordinary solution between a salt of an acid of formula I and a salt of the desired pharmaceutically acceptable cation.

Specifically, pharmaceutically acceptable salts of Formula I may be prepared by one or more of the following methods.

1. Reaction in a polar medium of a compound of formula XXIII.

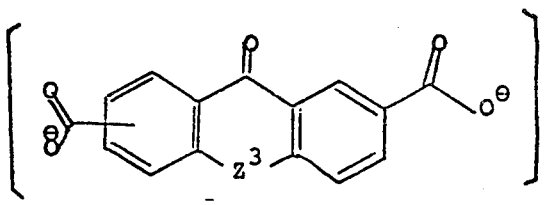

(XXIII)

wherein one of $Y^7$ and $Y^8$ is the hydrogen ion and the other represents the hydrogen ion or a cation of the desired salt, with a base of the desired salt, or when $Y^7$ and $Y^8$ represent together or separately a single or two cations other than the cation of the desired salt, and $Z^3$ has the meaning in formula I.

2. Reaction in a polar medium of a compound of formula XXIV

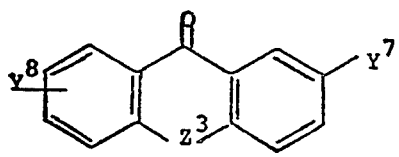

(XXIV)

wherein $Y^7$ and $Y^8$ are the same or different and each is selected from a carboxylic group and a group $Y^1$ as defined hereinbefore in formula XI, and $Z^3$ has the same meaning as before, with an appropriate Brønsted base and, when the Brønsted base does not contain a hydroxyl ion, in the presence of water. Examples of appropriate Brønsted bases are alkali and alkaline earth metal oxides and hydroxides for producing corresponding alkali and alkaline earth metal salts of formula I. Preferably the reaction is effected with heating.

Salts of formula I may be isolated from a reaction medium by any conventional process for the isolation of salts from a solution thereof in a polar medium. Thus the salts may be isolated by precipitation of the salt or by removal of the polar medium.

Precipitation of the salt may be effected by mixed solvent crystallisation or by the addition of excess base or salt thereof so as to produce a concentration of the cation of the salt to be isolated, substantially in excess of the molar ratio thereof in said salt to be isolated.

Mixed solvent crystallisation may be effected by addition, to a solution of a salt of formula I in a polar medium, of a second polar solvent other than, but miscible with, the polar solvent already present and in which second solvent the salt of formula I is less soluble than in the polar solvent already present.

Removal of the polar medium may be effected by evaporation, for example, by freeze-drying, or by azeotropic distillation.

Desirably the salts of formula I are purified prior to incorporation in a pharmaceutical composition. Purification may be effected by any conventional method. A particularly valuable purification process comprises isolation of a crude solid salt of formula I from a reaction mixture wherein said salt has been produced, by any method for the isolation of salts of formula I as described hereinabove; dissolution of the salt in hydrochloric acid; recovery of the corresponding acid of formula I as a solid; neutralisation of the acid of formula I with a Brønsted base of which base the cation is the cation of the required salt of formula I; removal of solid impurities by filtration; and isolation of the salt of formula I by a method as described hereinabove.

Conveniently an acid of formula I may be purified prior to neutralisation, by recrystallisation or by isolation of a N,N-dimethylformamide adduct and subsequently heating the adduct to drive off the N,N-dimethylformamide.

Esters and amides of acids of formula I may be prepared by any conventional method including esterification of the acid or acid chloride with an alkyl alcohol to yield the corresponding alkyl ester, and reaction of the acid or acid chloride with ammonia or an alkylamine to yield the corresponding amide or N-alkyl substituted amide respectively. Compounds of formula I where $Z^1$ and $Z^2$ are different and are chosen from acid, ester, amide and salt functions, may be prepared by the above methods, and by partial hydrolysis where appropriate.

The compounds of formula I are useful in the treatment or prophylaxis of mammalian allergic conditions such as asthma and other allergic chest conditions, hay fever (allergic rhinitis), conjunctivitis, urticaria and eczema. In particular they are of value in reaginic antibody mediated Type I hypersensitivity asthma ('extrinsic asthma') and the so-called 'intrinsic asthma' in which no sensitivity to extrinsic antigen can be shown.

The magnitude of a prophylactic or therapeutic dose of a compound of formula I will of course vary with the nature and the severity of the allergic condition to be treated and with the particular compound of formula I and its route of administration. In general the dose range lies within the range of 2 μg. to 100 mg. per kg. body weight of a mammal.

In the case of an allergic condition as defined hereinbefore, for example, allergic asthma, a suitable dosage is from 5 μg. to 0.5 mg., preferably from 20 μg. to 0.2 mg., for example about 0.1 mg., of a compound of formula I, per kg. of bodyweight of the patient undergoing treatment, when pulmonary administration as described hereinafter is employed. In the case where a composition for intravenous administration is employed a suitable dosage range is from 0.2 to 100 mg. of a compound of formula I per kg. of bodyweight of patient, and in the case where an oral composition is employed a suitable dosage range is from 2 to 50 mg. of a compound of formula I per kg. of bodyweight of a patient.

In the case where a composition for nasal administration is employed, for example, in the treatment of allergic rhinitis, a suitable dose is from 2 μg to 4 mg. of a compound of formula I per kg. of body weight of patient.

In the case of fluorenone-2, 7 dicarboxylate salts, particularly suitable dosages for the treatment of allergic asthma have been found to be as follows, all doses being given on the basis of the weight of the free dicarboxylic acid and as amounts per kg. of bodyweight of the patient undergoing treatment: for allergic asthma by pulmonary administration 20 μg to 0.2 mg. preferably 0.1mg., by intravenous administration 1 to 10mg. and by oral administration 10 to 40mg.; and for allergic rhinitis by nasal administration 10 μg to 0.4mg.

The pharmaceutical compositions of the present invention comprise a compound of formula I as an active ingredient, and may also contain pharmaceutically acceptable carrier and optionally other therapeutic ingredients. The compositions include composition suitable for oral, rectal, opthalmic, pulmonary, nasal, dermal, topical, or parenteral (including subcutaneous, intramuscular and intravenous) administration, although the most suitable route in any given case will depend on the nature and severity of the condition being treated, and on the nature of the active ingredient. They may be conveniently presented in unit dosage form and prepared by any of the methods well known in the art of pharmacy.

Pharmaceutical compositions of the present invention suitable for oral administration may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more accessory ingredients. In general the compositions are prepared by uniformly and intimately admixing the active ingredient with liquid carriers or finely divided solid carriers or both, and then, if necessary, shaping the product into the desired presentation. For example a tablet may be prepared by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Desirably, each tablet contains from 200mg. to 500mg. of the active ingredient, and each cachet or capsule contains from 500 to 2000mg. of the active ingredient.

A particularly valuable form of a pharmaceutical composition of the present invention, for use in the treatment of allergic asthma, is a composition suitable for pulmonary administration via the buccal cavity; although of course conditions other than allergic asthma may also be treated by pulmonary administration of the composition.

Preferably the composition is such that particles having a diameter of 0.5 to 7μ; most preferably 1 to 6μ, containing active ingredient, are delivered into lungs of a patient. This ensures that a maximal amount of active ingredient is administered to the alveolar sacs of the lungs and retained therein thus producing a maximal effect in the patient. Such compositions are most preferably in the form of dry powders for administration from a powder inhalation device or self-propelling powder-dispensing compositions.

Most preferably the powders of the pulmonary compositions as described hereinabove and hereinbelow comprise particles containing active ingredient of which particles at least 98% by weight have a diameter greater than 0.5μ and at least 95% by number have a diameter less than 7μ. Most desirably at least 95% by weight of the particles have a diameter greater than 1μ and at least 90% by number of the particles have a diameter less than 6 μ.

The compositions in the form of dry powders preferably comprise particles containing the solid active ingredient, the particles having a diameter of 0.5 to 7μ most preferably 1 to 6μ. Preferably these compositions include a solid diluent in the form of a fine powder. These compositions may be conveniently presented in a pierceable capsule of a pharmaceutically acceptable material, for example gelatin. Such compositions may be conveniently prepared by comminution of solid active ingredient optionally with a solid diluent. If desired the resulting powder may be filled into a pierceable capsule of a pharmaceutically acceptable material.

Other valuable forms of a composition of the present invention that are suitable for pulmonary administration are self-propelling compositions. These self-propelling compositions may be either powder-dispensing compositions or compositions dispensing the active ingredient in the form of droplets of a solution or suspension.

Self-propelling powder-dispensing compositions preferably comprise dispersed particles of solid active ingredient, having a diameter of 0.5 to 7μ most preferably 1 to 6μ and a liquid propellant having a boiling point of below 65°F at atmospheric pressure. The liquid propellant may be any propellant known to be suitable for medicinal administration and may comprise one or more lower alkyl hydrocarbons, or halogenated lower alkyl hydrocarbons, or mixtures thereof. Chlorinated and fluorinated lower alkyl hydrocarbons are especially preferred as propellant. Generally the propellant may constitute 50 to 99.9% w/w of the composition whilst the active ingredient may constitute 0.1 to 20% w/w, for example, about 2% w/w, of the composition.

The pharmaceutically acceptable carrier in such self-propelling compositions may include other constituents in addition to the propellant, in particular a surfactant or a solid diluent or both. Surfactants are desirable in preventing agglomeration of the particles of active ingredient and in maintaining the active ingredient in suspension. Especially valuable are liquid non-ionic surfactants and solid anionic surfactants or mixtures thereof. Suitable liquid non-ionic surfactants are those having a hydrophile-lipophile balance (HLB, see Journal of the Society of Cosmetic chemists Vol. 1 pp. 311–326 (1949)) of below 10, in particular esters and partial esters of fatty acids with aliphatic polyhydric alcohols, for instance, sorbitan monooleate and sorbitan trioleate, known commercially as "Span 80" (Trade Name) and "Span 85" (Trade Name). The liquid non-ionic surfactant may constitute up to 20% w/w of the composition, though preferably it constitutes below 1% w/w of the composition. Suitable solid anionic surfactants include alkali metal, ammonium and amine salts of dialkyl sulphosuccinate, where the alkyl groups have 4 to 12 carbon atoms, and alkylbenzene sulphonic acid where the alkyl group has 8 to 14 carbon atoms. The solid anionic surfactants may constitute up to 20% w/w of the composition, though preferably below 1% w/w of the composition.

Solid diluents may be advantageously incorporated in such self-propelling compositions where the density of the active ingredient differs substantially from the density of the propellant; also in order to help to maintain the active ingredient in suspension. The solid diluent is in the form of a fine powder, preferably having a particle size of the same order as that of the particles of active ingredients. Suitable solid diluents include sodium choride and sodium sulphate.

Compositions of the present invention may also be in the form of a self-propelling composition wherein the active ingredient is present in solution. Such self-propelling compositions may comprise an active ingredient, propellant and co-solvent, and advantageously an antioxidant stabiliser. The propellant is one or more of those already cited above. Co-solvents are chosen for their solubility in the propellant, their ability to dissolve the active ingredient, and for their having the lowest boiling point consistent with these above-mentioned properties. Suitable co-solvents are lower alkyl alcohols and ethers and mixtures thereof. The co-solvents may constitute 5 to 40% w/w of the composition, though preferably less than 20% w/w of the composition.

Antioxidant stabilisers may be incorporated in such solution-compositions to inhibit deterioration of the active ingredient and are conveniently alkali metal ascorbates or bisulfites. They are preferably present in an amount of up to 0.25% w/w of the composition.

Such self-propelling compositions may be prepared by any method known in the art. For example the active ingredient either as particles as defined hereinbefore in suspension in a suitable liquid or in up to 20% w/v solution in an acceptable co-solvent as appropriate, is mixed with any other constituents of a pharmaceutically acceptable carrier. The resulting mixture is cooled and introduced into a suitable cooled container and propellant is added therto in liquid form; and the container is sealed.

Alternatively, such self-propelling compositions may be prepared by mixing the active ingredient either in particles as hereinbefore defined or in 2 to 20% w/v alcohol or aqueous solution as appropriate, together with the remaining constituents of the pharmaceutically acceptable carrier other than propellant; introducing the resulting mixture, optionally with some propellant, into a suitable container; sealing the container; and injecting propellant under pressure into the container at ambient temperature through a valve which comprises a part of the container and is used to control release of the composition from it. Desirably the container is purged by removing air from it at a convenient stage in the preparation of the self-propelling composition.

A suitable container for a self-propelling composition, is one provided with a manually operable valve and being constructed of aluminium, stainless steel or reinforced glass. The valve should of course be one having the desired spray characteristic, that is, the spray issuing from the valve should have the characteristics of particle size as hereinbefore defined. Advantageously the valve is of the metered type, that is a valve of the type which delivers a fixed amount of composition on the occasion of each operation of the valve, for example, about 50 or 100 microliters of composition in each delivery.

Compositions of the present invention may also be in the form of aqueous or dilute alcoholic solution, optionally a sterile solution, of the active ingredient for use in a nebuliser or atomiser, wherein an accelerated air stream is used to produce a fine mist consisting of small droplets of the solution. Such compositions usually contain a flavouring agent such as saccharin sodium and a volatile oil. A buffering agent such as sodium phosphate; an antioxidant such as sodium metabisulfite; and a surface active agent may also be included in such a composition. Desirably such a composition should contain a preservative such as methylhydroxybenzoate.

Compositions of the present invention suitable for parenteral administration conveniently comprise sterile aqueous solutions of the active ingredient, which solutions are preferably isotonic with blood of a patient under treatment. These are preferably administered intra-venously, although administration may also be effected by means of subcutaneous or intra-muscular injection. Such compositions may be conveniently prepared by dissolving solid active ingredient in water to produce an aqueous solution, and rendering said solution sterile and isotonic with human blood.

Pharmaceutical compositions of the present invention suitable for topical use include compositions suitable for administration to the skin, eyes, nose and mouth.

Compositions for use on the skin include lotions and creams comprising liquid or semi-solid emulsions, either oil-in-water or water-in-oil, which preferably contain from 0.2 to 5% w/v of the active ingredient. Ointments comprising 0.2 to 5% w/v of the active ingredient dissolved or dispersed in a semi-solid basis may also be used for topical administration to the skin. Conveniently the semi-solid basis contains liquid or semi-solid hydrocarbons, animal fat, wool alcohol or a macrogol, possibly with an emulsifying agent. Desirably the creams and ointments should contain a preservative such as methyl hydroxybenzoate.

Compositions for administration to the eye include eye drops comprising the active ingredient in an aqueous or oily solution, preferably at a concentration of 0.2 to 5% w/v. Such solutions are desirably fungistatic and bacteriostatic and are preferably prepared sterile. Compositions for administration to the eye also include eye ointments which preferably comprise the same concentration of active ingredient, conveniently in the form of a salt, either dissolved in one of the ingredients of the semi-solid basis of the ointment or as a finely divided suspension therein.

Compositions suitable for administration to the nose include powder self-propelling and spray compositions similar to those already described under compositions suitable for pulmonary administration but having when dispersed, a somewhat larger particle size of the order of 10 to 200 microns. In the case of self-propelling solution and spray compositions this effect may be achieved by choice of a valve having the desired spray characteristic i.e. being capable of producing a spray having the desired particle size or by incorporating the medicament as a suspended powder of controlled particle size. Thus the composition instead of passing into the lungs is largely retained in the nasal cavity. Other compositions suitable for nasal administration include a coarse powder having a particle size of 20 to 500 microns which is administered in the manner in which snuff is taken i.e. by rapid inhalation through the nasal passage from a container of the powder held close up to the nose. Another composition suitable for nasal administration is nasal drops comprising 0.2 to 5% w/v of the active ingredient in aqueous or oily solution.

Compositions suitable for topical administration in the mouth include lozenges comprising 10 to 100mg. of the active ingredient in a flavoured basis, usually sucrose and acacia or tragacanth; and pastilles comprising 10 to 100mg. of the active ingredient in an inert basis such as gelatin and glycerine; or sucrose and acacia.

Other therapeutic ingredients suitable for inclusion in the hereinbefore described compositions, especially in the case of those compositions intended for use in the treatment of allergic asthma, include bronchodilators. Any bronchodilator may be used in such a composition although particularly suitable bronchodilators are isoprenaline, adrenaline, orciprenaline isoethanine and physiologically acceptable acid addition salts thereof, especially isoprenaline sulphate. Conveniently the bronchodilator is present in the composition in an amount of 0.1 to 50% w/w of the weight of active ingredient present.

The present invention provides pharmaceutical compositions comprising a compound of formula I as defined hereinbefore together with a pharmaceutically acceptable carrier thereof.

Accordingly, the present invention provides a method of treatment of an allergic condition as hereinbefore defined comprising administration of a prophylactic or a therapeutic dose of a compound of formula I.

In another aspect the present invention provides a self-propelling pharmaceutical composition comprising 0.1 to 20% w/w of a compound of formula I as defined hereinbefore in the form of solid particles having a diameter of from 1 to 7$\mu$, 0.01 to 20% w/w of surfactant and 50 to 99.9% w/w of a liquid propellant having a boiling point of below 19°C at atmospheric pressure.

In further aspects the present invention provides:

compositions comprising a tricyclic compound of formula II or III as defined hereinbefore in association with a pharmaceutically acceptable carrier therefor;

The novel tricyclic compounds of formula VI as defined hereinbefore; and the novel solid tricyclic compounds of formula X, as defined hereinbefore.

In another aspect the present invention provides a method of preparing a pharmaceutical formulation suitable for use in the treatment in mammals of allergic conditions as defined hereinabove characterised in that one prepares a compound of formula I by any one of the processes described hereinabove; and optionally converts a compound of formula I so-produced to another compound of formula I; and admixes a compound of formula I so-produced with an inert carrier therefor.

The following preparations and examples illustrate the methods for preparing compounds in accordance with the present invention, as well as compounds and compositions of the present invention. In the examples and preparations, all temperatures are in degrees Celsius. Where melting points are not given for compounds of formula I, the compounds decompose at temperatures below their melting points and/or their melting points are at temperatures above those readily determinable by conventional techniques.

REFERENCE PREPARATION 1

Fluorenone-2,6-dicarboxylic acid

Aluminium chloride (440 g), suspended in dry 1,2-dichloroethane (500 ml), was stirred and treated dropwise, at 0°C, with acetic anhydride (162 ml, 175 g). The resulting solution was then added, with stirring at 0°C, to a solution of fluorene (125 g) in 1,2-dichloroethane (700 ml). When the addition was completed, half of the dichloroethane was removed under reduced pressure and the residue was poured into a mixture of ice and 2N-hydrochloric acid. The resulting solid was collected by filtration, washed with water, dried and recrystallised from acetone to give 2,7-diacetylfluorene, m.p. 177–180°.

Finely ground 2,7-diacetylfluorene (75.6 g) was added to a stirred solution of sodium hydroxide (14 g) in 4.5% aqueous sodium hypochlorite (3.5 liter). The mixture was heated to 80°C for 5 hours and then cooled and filtered. The solid thus obtained was treated with hot water (1 liter), filtered to remove unreacted 2,7-diacetylfluorene, and the filtrate washed twice with dichloromethane and then acidified with concentrated hydrochloric acid. The resulting pale yellow precipitate was filtered, washed well with water and dried, to give pure fluorenone-2,7-dicarboxylic acid, m.p. 410°C (decomp).

REFERENCE PREPARATION 2

Anthraquinone-2,6-dicarboxylic acid

Sodium nitrite (6.82 g.) was added to concentrated sulphuric acid (54.1 ml) at 0°C with vigorous stirring and external cooling. The solution was warmed to 50°–60°C and 2,6-diaminoanthraquinone (11.60 g.) was added in small portions with stirring. The reaction mixture was heated at 50°–60°C for 30 minutes, cooled to 30°C and poured onto ice (150g.). The yellow tetrazonium salt was filtered off and washed with a little cold water.

Cuprous cyanide solution was prepared according to the method in "A Text Book of Practical Organic Chemistry" p. 584, A. I. Vogel, Longmans (1948), from cupric sulphate pentahydrate (17g.), sodium metabisulphite (4.70 g.) and potassium cyanide (4.70g.).

To the cuprous cyanide solution was added the solid tetrazonium salt in small portions at 60°–70°C. Frothing due to the evolution of nitrogen occured. When the addition was complete, the reactants were heated on a steam bath for 25 minute to complete the reaction. The crude nitrile was filtered off as a brown solid, washed with water, and dried in an oven at about 90°C. Infrared spectrum (KBr disc) confirmed the presence of nitrile ($\nu$ C $\equiv$ N 2100 cm$^{-1}$).

Due to the very low solubility of the crude nitrile in common solvents, it was not possible to purify the nitrile by recrystallisation. Accordingly the crude nitrile was hydrolysed directly by boiling with aqueous sodium hydroxide (40g. in 300 ml. of water), for 7 hours. After cooling the reaction mixture was acidified with excess dilute hydrochloric acid, and the crude acidic product filtered off and washed with water.

Three recrystallisations from dimethylformamide yielded pure anthraquinone-2,6-dicarboxylic acid (1.37g.) after drying at 156°C under pressure of 15 mm. of mercury in a drying pistol. The melting point was above 400°C.

REFERENCE PREPARATION 3

Anthraquinone-2,6-dicarboxylic acid 2,6-Dimethylanthracene (3.09g.), sodium dichromate (21.0g.) and water (75 ml.) were heated together at 215°C in an autoclave for 20 hours. The resulting mixture was filtered to remove chromic oxide and the liquors acidified with excess hydrochloric acid. The precipitated acid was filtered off and dried to yield a dark brown solid (1.14g.). The crude material was recrystallised from dimethylformamide and dried at 156°C under a pressure of 15 mm. of mercury to yield anthraquinone-2, 6-dicarboxylic acid.

REFERENCE PREPARATION 4

Anthraquinone-2,6-dicarboxylic acid 2,6-Dimethylanthraquinone (15.4g.), chromium troxide (78.0g.) and glacial acetic acid (675 ml.) were boiled together under reflux for 64 hours. On cooling the product crystallised out and was filtered off and washed with water. The crude acid was recrystallised from dimethylformamide and dried at 110°C for 3 days to yield anthraquinone-2,6-dicarboxylic acid. Chemical analysis of the product: found Carbon 64.69% and Hydrogen 3.15% by weight.

REFERENCE PREPARATION 5

Fluorenone-2-carboxylic acid

A solution of 2-acetylfluorene (86 g.) in acetic acid (1075 ml.) at 60° was treated slowly with sodium dichromate (1020 g.), and then with acetic anhydride (285 ml.). The mixture was heated to reflux with stirring for 3 hours, cooled and poured into water (6 l.), and the precipitate was filtered and washed well with water. This solid was warmed with N-sodium hydroxide (520 ml.) and the mixture was filtered. The aqueous filtrate was washed three times with dichloromethane (3 × 60 ml.) and then heated on the steam-bath and cautiously acidified with hydrochloric acid. The yellow product was filtered, washed well with water and dried in vacuo to give fluorenone-2-carboxylic acid m.p. > 300°.

REFERENCE PREPARATION 6

Anthraquinone-2-carboxylic acid

2-Methylanthraquinone (3 g.) was dissolved in sulphuric acid (15 ml) and the solution cooled and diluted with water (15 ml). The mixture was then cooled and stirred vigorously during the portionwise addition of powered sodium dichromate (9 g.) and finally heated on the steam-bath for 3 hours, cooled and treated with water (100 ml.). The precipitated solid was filtered washed well with water and treated with hot dilute aqueous ammonia (60 ml. water and 2 ml. of 0.880 ammonia). The solution was filtered hot and acidified with hydrochloric acid; the pale yellow precipitate was filtered, washed with water and dried to give anthraquinone-2-carboxylic acid, m.p. 291°–292° unchanged by recrystallisation from dimethylformamide.

REFERENCE PREPARATION 7

Anthraquinone-2,7-dicarboxylic acid 2,7-Dimethyl anthraquinone (5.15g, 21.8 m.mole) was refluxed with chromium trioxide (26.00g, 200% excess) in glacial acetic acid (250 ml) for 65 hours. The dark green solution was cooled in an ice-bath and the deposited material was filtered off. This was washed with glacial acetic acid, and then with water to give a pale green solid which was dried at 100°.

The crude material was then recrystallised from boiling dimethylformamide, treated with decolorising charcoal, and filtered at the boil. The solid which separated on cooling was filtered off, washed with a little ice-cold dimethylformamide, and dried under vacuum at 155°C. The product, anthraquinone-2, 7-dicarboxylic acid, had a m.p. 399°–401°(decomp.).

REFERENCE PREPARATION 8

Methyl fluorenone-2-carboxylate

Fluorenone-2-carboxylic acid (3 g.) in dry methanol (150 ml.) was treated with sulphuric acid and the mixture was refluxed with stirring for 72 hours and allowed to cool. The yellow precipitate was filtered, washed well with methanol, then with water, and dried to give methyl fluorenone-2-carboxylate, m.p. 182°–185°.

REFERENCE PREPARATION 9

7-Nitrofluorenone - 2 -carboxylic acid

A solution of 2-acetyl-7-nitrofluorene (1.4g) in acetic acid (100ml) was treated protionwise with sodium dichromate (6.85g.), then with acetic anhydride (5ml), and heated to reflux for 8 hours. The reaction mixture was cooled somewhat, poured into hot water (600ml) and then cooled and filtered. The resulting solid was warmed with 0.5% aqueous potassium hydroxide and filtered hot, to give a filtrate which was acidified with hydrochloric acid. The precipitated acid was separated by filtration, washed well with hot water and dried in vacuo to give 7-nitrofluorenone-2-carboxylic acid, m.p. 325°–327°.

REFERENCE PREPARATION 10

Disodium anthraquinone-2,6-dicarboxylate

Anthraquinone-2,6-dicarboxylic acid (0.50g) was dissolved in sodium carbonate solution (1 equivalent of sodium carbonate, 0.18g, in water, 100 ml) with warming. As the di-sodium salt did not separate on cooling, the solution was evaporated to approximately ⅓ volume and heavily diluted with ethanol. The solid which separated was filtered off, dried at 100°C. and analysed for the dihydrate. Analysis:
Required Carbon 51.09, Hydrogen 2.68,
Found Carbon 50.67, Hydrogen 2.78.

REFERENCE PREPARATION 11

7-Methoxyfluorenone-2-carboxylic acid

A suspension of 2-acetyl-7-methoxyfluorene (1.2g.) in a solution of 5% aqueous sodium hypochlorite (50ml.) containing sodium hydroxide (200mg.) was stirred and heated for 5 hours at 80°, and then cooled to 0° and filtered, the filtrate being discarded. The precipitate consisted of starting material and the sodium salt of the product: it was treated with hot water (50ml., 25ml and 25ml, successively) and filtered hot; the combined filtrates were acidified with hydrochloric acid and the precipitate was filtered, washed with water and dried in vacuo. Recrystallisation from a mixture of dimethylformamide and ethanol gave 7-methoxyfluorenone-2-carboxylic acid, mp. >300°.

REFERENCE PREPARATION 12

Fluorenone-2,7-dicarboxamide

Flourenone-2,7-dicarboxylic acid (20g.) was suspended in thionyl chloride (275ml.) containing dimethylformamide (1m.) and the mixture was heated to reflux for 3 hours. The resulting solution was evaporated to dryness under reduced pressure and the residual solid was recrystallised from toluene (200ml.). A portion (2g.) of this material was added to a mixture of 0.880 ammonia solution (7ml.) and water (7ml.), and stirred for 36 hours at room temperature. The total mixture was then stirred at 100° for 4 hours; the solid was filtered suspended in water (100ml.) and heated to 100° for 8 hours. Finally, this mixture was cooled and the solid was filtered, washed with water and dried to give fluorenone-2,7-dicarboxamide mp. >300°.

REFERENCE PREPARATION 13

Dimethyl fluorenone-2,7-dicarboxylate

A mixture of fluorenone-2,7-dicarboxylic acid (10g.), dry methanol (400ml.) and concentrated sulphuric acid (4ml.) was stirred and heated to reflux for 72 hours. The mixture was cooled and filtered and the solid was washed with methanol then with water, and dried in vacuo to give dimethyl fluorenone-2,7-dicarboxylate, mp. 223°–224°.

REFERENCE PREPARATION 14

7-Acetylfluorenone-2-carboxylic acid

This compound was prepared in known manner (Chemical Abstracts 1935, 29, 1084 1) and had a mp. >300°.

EXAMPLE 1

Disodium fluorenone-2,7-dicarboxylate

Fluorenone-2,7-dicarboxylic acid (10 g) was stirred with "Analar" (Trade Name) sodium bicarbonate (6.28 g) and water (300 ml); warming gave a clear yellow solution which was evaporated under reduced pressure to ca. 50 ml and treated with warm ethanol (500 ml). The resulting pale yellow solid was collected and dried, to give disodium fluorenone-2,7-dicarboxylate monohydrate.
The product obtained, having the following formula:

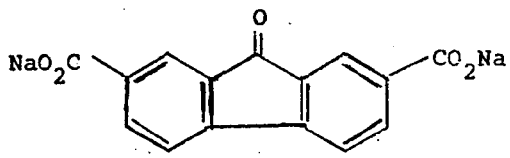

(Synonym: Disodium 9-oxofluorene-2,7-dicarboxylate) provided, when dispersed in Nujol Mull, the infrared spectrum shown in FIG. 1 appended hereto.

EXAMPLE 2

Dipotassium fluorenone-2,7-dicarboxylate

Fluorenone-2,7-dicarboxylic acid (0.534 g) was dissolved in warm water containing Analar (Trade Name) potassium carbonate (0.544 g). The yellow solution was concentrated, under reduced pressure, to 3 ml and treated with ethanol. The resulting pale yellow solid was collected and dried at ambient temperature and pressure to give hydrated dipotassium fluorenone-2,7-dicarboxylate.

EXAMPLE 3

Disodium fluorenone-2,7-dicarboxylate

A. Preparation of 2,7-Diacetylfluorene

Anhydrous aluminium chloride (872 g.) was suspended in 1,2-dichloroethane (750 ml.), the mixture stirred with cooling in an ice-salt bath, and acetic anhydride (282 ml.) added at such a rate as to maintain the internal temperature between 0° and 10°C. When the addition was complete a solution of fluorene (200 g.) in 1,2-dichloroethane (800 ml.) was added dropwise maintaining the temperature below 20°C. Upon completion of the addition, the cooling bath was removed and the mixture stirred for two hours at ordinary temperature, after which the cooling bath was replaced and sufficient 3N-hydrochloric acid added slowly to give two clear phases without any solid in suspension.

The mixture was distilled under reduced pressure to remove all of the organic solvent and the solid collected by filtration; the crude product was washed thoroughly with water on the filter and dried in an oven at about 100°C, before crystallising from boiling toluene to give 2,7-diacetylfluorene m.p. 180°C.

B. Preparation of Disodium salt of fluorenone-2,7-dicarboxylic acid

Finely ground 2,7-diacetylfluorene (30 g.) was suspended in sodium hypochlorite solution (1.0 l.; about 8% available chlorine) and the stirred suspension heated to 90°C. Heating was continued for 5 hours allowing the chloroform formed in the reaction to distil out. At the end of the 5 hours sodium chloride (100 g.)

was added and the stirred suspension cooled to about 30°C and the solid collected by filtration. The solid was transfered to a flask, water (500 ml.) added, heated to about 80°C and the solution filtered to remove unreacted 2,7-diacetylfluorene. The filtrate was warmed to 40°C and an excess of sodium chloride added to precipitate the disodium salt of fluorenone-2,7-dicarboxylic acid.

EXAMPLE 4

Fluorenone-2,7-dicarboxylic acid, disodium salt

Fluorenone-2,7-dicarboxylic acid (30 g.) was suspended in water (300 ml.) with stirring and neutralised with sodium hydroxide solution (about 10%).

Charcoal (3 g.) was added to the solution and stirred at ambient temperature for 30 minutes, after which the mixture was filtered through a Hyflo (Trade Name) bed.

The filtrate was placed in a clean beaker and 1200 ml. of filtered methanol added to precipitate the solid disodium salt which was collected by filtration, suspended with stirring in filtered methanol, collected, washed with methanol and dried at 100°C in a vacuum oven to give solid disodium fluorenone-2,7-dicarboxylate.

EXAMPLE 5

Fluorenone-2,7-dicarboxylic acid monosodium salt

Figure 2:
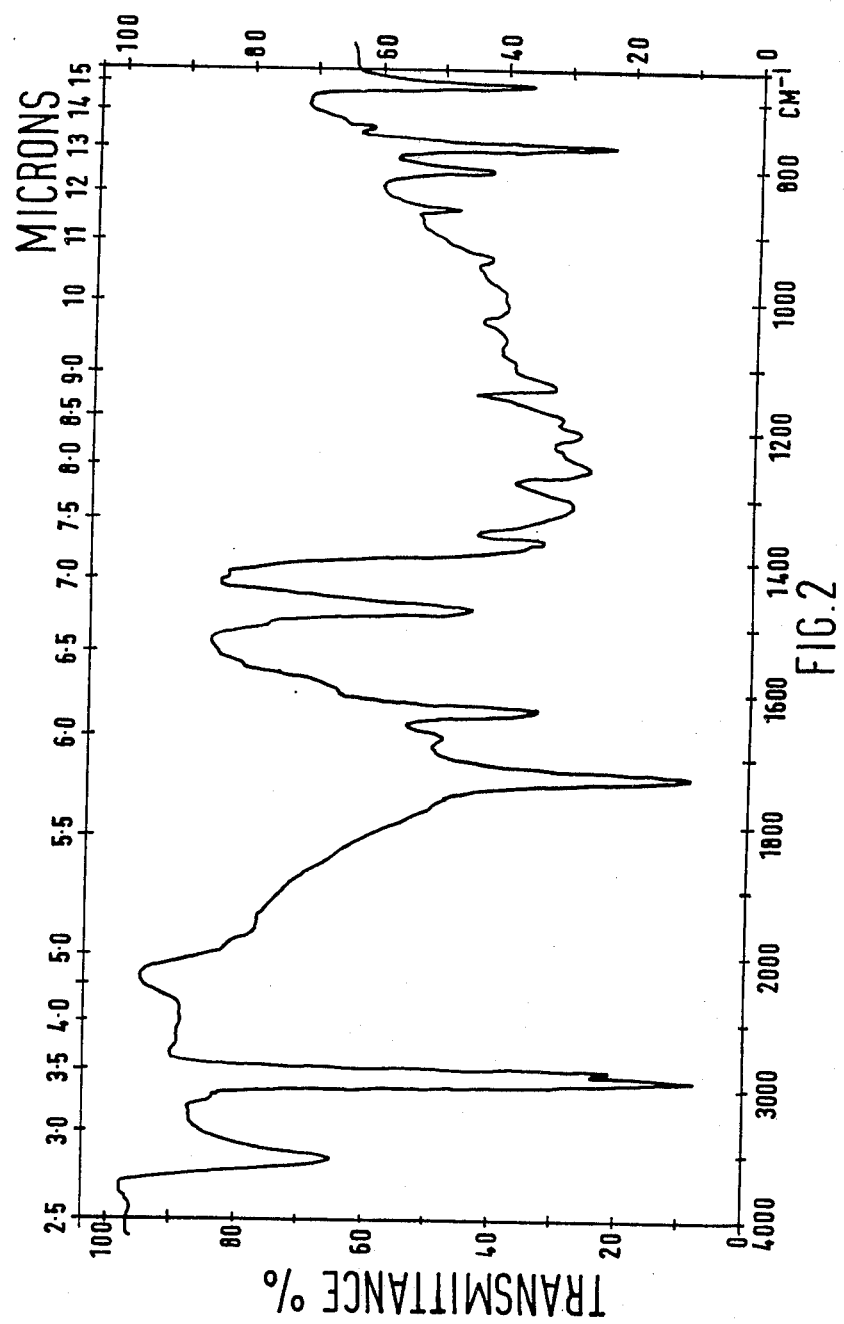

Fluorenone-2,7-dicarboxylic acid disodium salt monohydrate (9.906 g.) was dissolved in water (50 ml.) The solution was stirred and treated during 15 minutes with successive drops of 5N hydrochloric acid (6 ml), stirred for a further 15 minutes at room temperature and then for 1 hour at 50°C. The mixture was cooled and filtered and the pale yellow solid was washed and dried in vacuo to give fluorenone-2,7-dicarboxylic acid monosodium salt monohydrate, which when dispersed in Nujol Null, provided the infra-red spectrum shown in FIG. 2 appended hereto.

EXAMPLE 6

Fluorenone-2,7-dicarboxylic acid calcium salt

Figure 3:
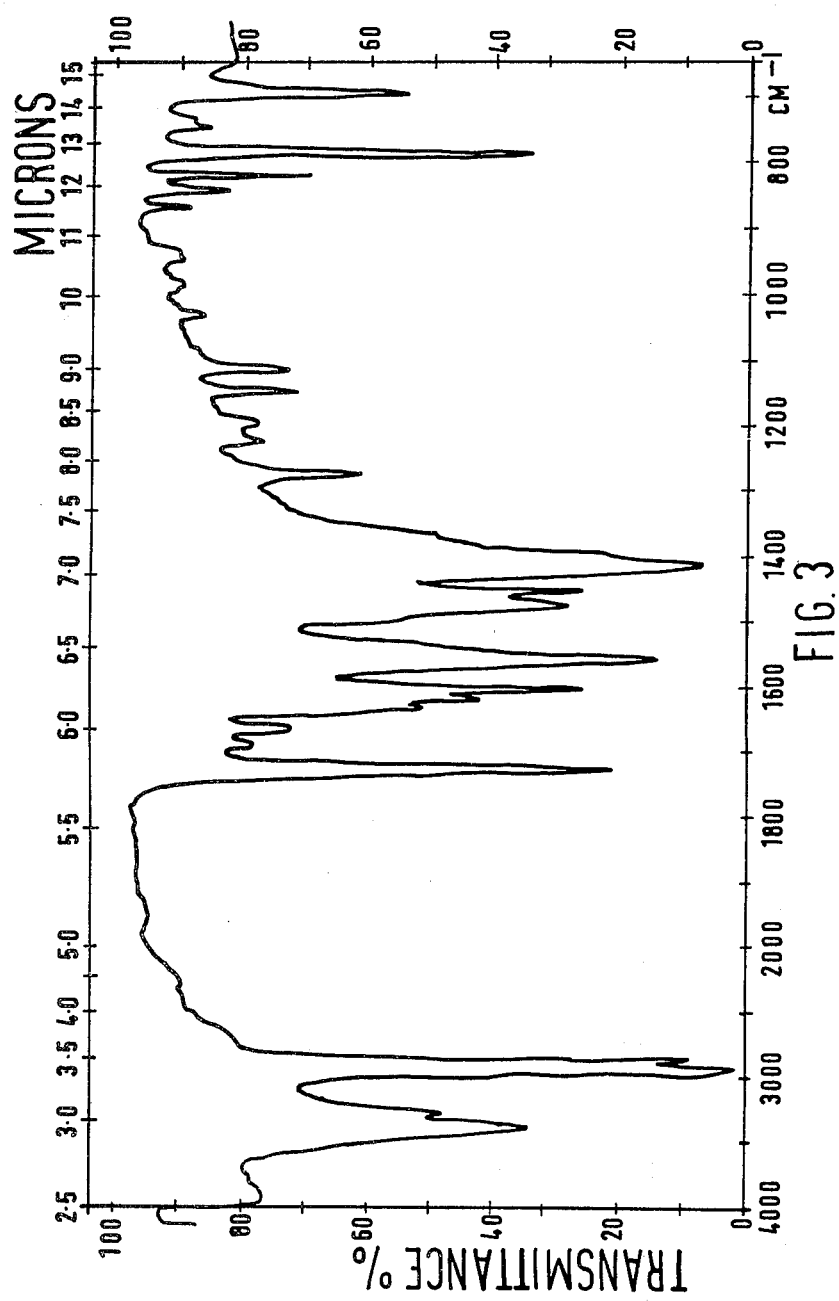

Fluorenone-2,7-dicarboxylic acid disodium salt monohydrate (2 g.) was dissolved in water (10 ml) with gentle warming, stirred and treated with a solution of calcium nitrate (3 g.) in a little water. The mixture was warmed for a few minutes and the pale yellow precipitate was filtered, washed with water, and dried at ambient temperature and pressure to give fluorenone-2,7-dicarboxylic acid calcium salt dihydrate, which when dispersed in Nujol Mull, provided the infra-red spectrum in FIG. 3 appended hereto.

EXAMPLE 7

Fluorenone-2,7-dicarboxylic acid disodium salt

Figure 4:
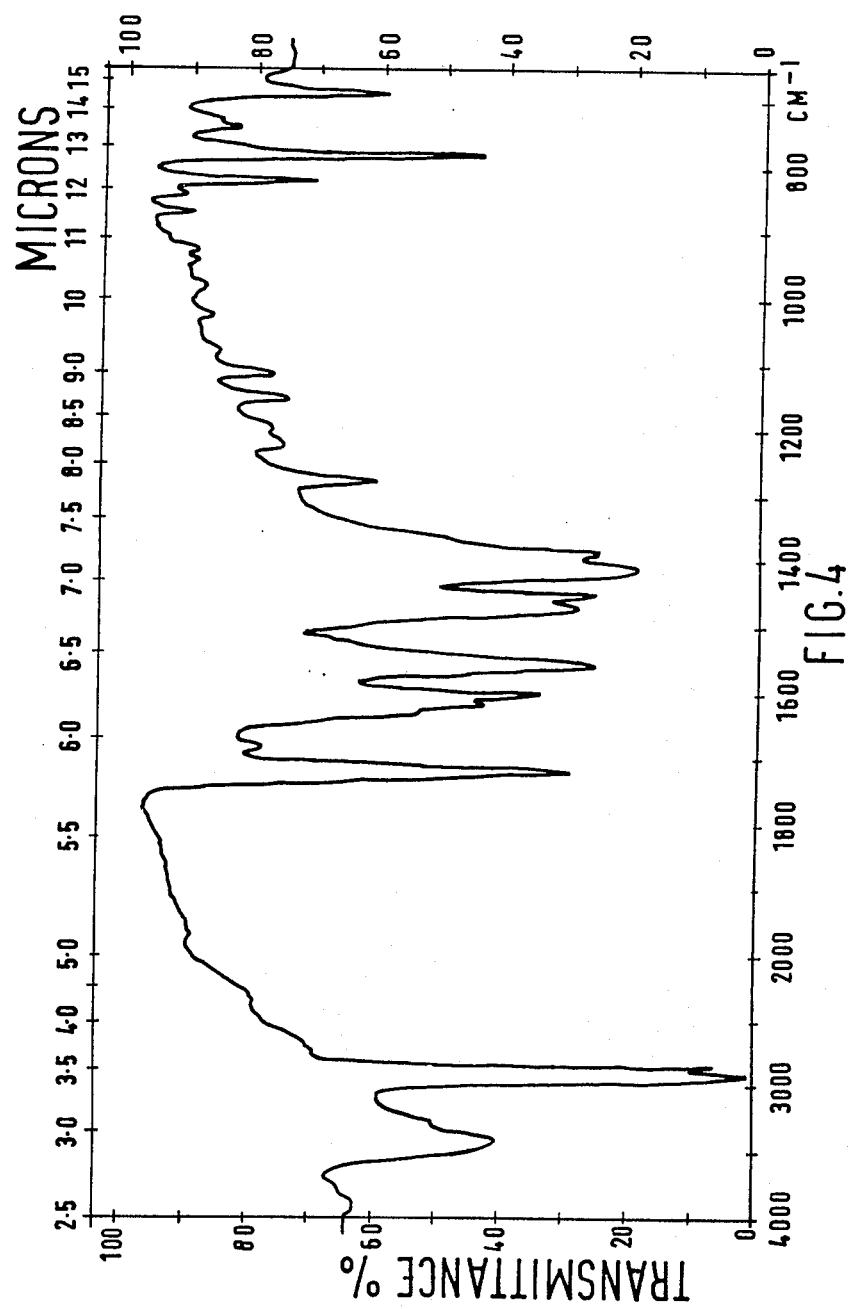

A solution of fluorenone-2,7-dicarboxylic acid disodium salt monohydrate (2 g.) in warm water (10 ml.) was stirred and treated with magnesium nitrate (1.7 g.) dissolved in water. The resulting pale yellow precipitate was filtered, washed with water, and dried at ambient temperature and pressure to give fluorenone-2, 7-dicarboxylic acid magnesium salt dihydrate which when dispersed in Nujol Mull, provided the infra-red spectrum shown in FIG. 4 appended hereto.

EXAMPLE 8

Fluorenone-2,7-dicarboxylic acid dipotassium salt

Figure 5:
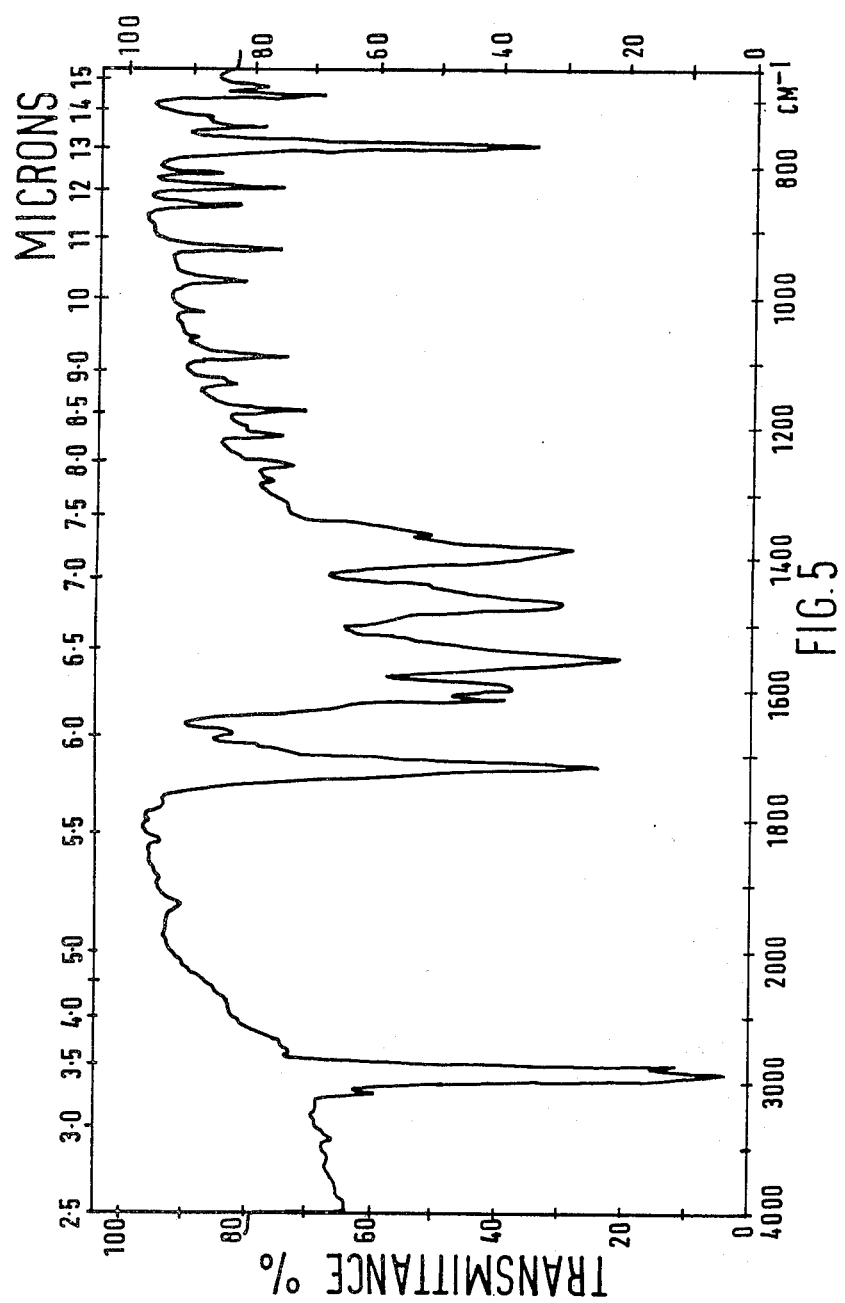

Fluorenone-2,7-dicarboxylic acid (4.0 g.) was added in portions to a stirred solution of potassium carbonate (2.06 g.) in water (30 ml.) and stirring was then continued overnight at room temperature. The resulting solution was treated with an excess of ethanol to precipitate a yellow solid which was filtered washed with ethanol, and dried in vacuo at 100° to give anhydrous fluorenone-2,7-dicarboxylic acid dipotassium salt, which when dispersed in Nujol Mull, provided the infra-red spectrum shown in FIG. 5 appended hereto.

EXAMPLE 9

Fluorenone-2,7-dicarboxylic acid diammonium salt

Fluorenone-2,7-dicarboxylic acid (2 g.) was suspended in water (40 ml), treated with an excess of 0.880 ammonia and warmed to 50°C with stirring. After 45 minutes the solid had dissolved and the solution was treated with ethanol (150 ml) and cooled to 0°C. The yellow solid was filtered and dried in vacuo to give anhydrous fluorenone-2,7-dicarboxylic acid diammonium salt, which when dispersed in Nujol Mull provided the infra-red spectrum shown in FIG. 6, appended hereto.

EXAMPLE 10

Fluorenone-2-carboxamide

Fluorenone-2-carbonyl chloride (2.5 g.) was added in one portion to rapidly stirred 0.880 ammonia (25 ml.). Stirring was continued for 3 hours at room temperature and then for 5 hours at 50°. The solid was filtered, washed with water, dried, and recrystallised from a mixture of dimethylformamide and ethanol to give deep yellow crystals of fluorenone-2-carboxamide, m.p. 252°–254°.

EXAMPLE 11

7-Chloro-fluorenone-2-carboxylic

2-Acetyl-7-chlorofluorene (4g.), dissolved in acetic acid (40 ml.) at 60°, was treated with sodium dichromate (25 g.) in ca. 5 g. portions. The mixture was refluxed for 5 hours, cooled and poured into cold water (1 l.). The precipitated solid was filtered, washed well with water and stirred at room temperature with a 10% solution (50 ml.) of 0.880 ammonia in water. The mixture was filtered and the solid re-extracted with a 2% solution (50 ml.) of 0.880 ammonia in water. Acidification of the combined ammoniacal extracts with sulphuric acid gave 7-chloro-fluorenone-2-carboxylic acid, m.p. > 300°.

EXAMPLE 12

7-Bromo-fluorenone-2-carboxylic acid

2-Acetyl-7-bromofluorene (4 g.) in hot acetic acid (40 ml.) was treated portionwise, over 45 minutes, with sodium dichromate (25 g.), then with acetic anhydride (7.5 ml). The mixture was heated to reflux for 5 hours and then worked up as described in the previous Example to give 7-bromo-fluorenone-2-carboxylic acid, m.p. > 300°.

EXAMPLE 13

7-Cyano-fluorenone-2-carboxylic acid

A mixture of 2-acetyl-7-bromofluorene (13.2 g.) and cuprous cyanide (8.2 g.) in quinoline (40 ml.) was heated to reflux for 40 minutes, cooled to 100° and poured into a mixture of ice-cold dilute aqueous ammonia and dichloromethane. The organic layer was separated, filtered to remove a yellow solid, washed with N-hydrochloric acid, dried over sodium sulphate and evaporated. The residual solid was recrystallised from ethanol containing a small amount of dimethylformamide to give 2-acetyl-7-cyanofluorene m.p. 182°–188°.

2-Acetyl-7-cyanofluorene (2.33 g.) was added to 5% aqueous sodium hypochlorite (160 ml.) containing sodium hydroxide (400 mg.) and chloroform (5 ml.) and the mixture was stirred at 70°–80° for 7 hours, and then cooled and filtered. The precipitate was separated, digested with hot water (200 ml.) and filtered hot to give a solution which was acidified with hydrochloric acid. The resulting solid was filtered, washed with hot water and dried in vacuo to give 7-cyanofluorenone-2-carboxylic acid m.p. > 300°.

EXAMPLE 14

7-Ethyl-fluorenone-2-carboxylic acid

Acetic anhydride (2.67 g.) in dichloroethane (10 ml.) was added deopwise to a stirred, cooled (0°) suspension of aluminum chloride (6.95 g.) in dichloroethane (20 ml.). Cooling and stirring were continued during the dropwise addition of a solution of 2-ethylfluorene (4.61 g.) in dichloroethane (50 ml.). The mixture was stirred for one hour at room temperature and then decomposed by the dropwise addition of 2N-hydrochloric acid (40 ml.) to the cooled solution. The organic layer was separated, washed with water and with aqueous sodium bicarbonate, dried over anhydrous sodium sulphate, filtered, and evaporated under reduced pressure. The residue was recrystallised from light petroleum (ca 250 ml., b.p. 60°–80°) to give 2-acetyl-7-ethylfluorene m.p. 120°–122°.

A solution of sodium hypochlorite was prepared by the dropwise addition of bromine (27.5 g., 9.4 ml.) to a cooled (0°), stirred solution of sodium hydroxide (17.2g.) in water (600 ml.). 2-Acetyl-7-ethylfluorene (6.74 g.) was added with stirring and the stirred mixture was warmed to 70°, maintained at this temperature for 5 hours and allowed to stand overnight at room temperature. The mixture was filtered and the filtrate was heated to 60° and treated with sodium acetate (300 g.). The sodium salt thus precipitated was filtered, dissolved in a minimum of hot water and converted to the free acid with hydrochloric acid. The product was filtered, washed well with water and dried in vacuo to give pure 7-ethylfluorenone-2-carboxylic acid m.p. > 300°, homogeneous by thin layer chromatography.

EXAMPLE 15

7-Butyl-fluorenone-2-carboxylic acid

A mixture of 2-butyrylfluorene (11.3 g.), powdered potassium hydroxide (4.16 g.) and 100% hydrazine hydrate (9 ml.) in ethylene glycol (104 ml.) was refluxed for 1 hour with stirring. The mixture was then slowly distilled until the boiling-point reached 185° and then heated to reflux for 3 hours. The cooled mixture was treated with water (ca. 300 ml.) and the product was isolated with ether in the usual manner. Recrystallisation from methanol gave 2-butylfluorene, m.p. 65°–66.5°.

2-Butylfluorene (6.1 g.) was acetylated exactly as described for 2-ethylfluorene in the preceding Example 21, using acetic anhydride (3.08 g.) and aluminium chloride (8.66 g.) in dichloroethane. The product was recrystallised from light petroleum to give 2-acetyl-7-butylfluorene, m.p. 102° 104.5°. This product (1.98 g.) was oxidised with sodium hypobromite (from 7.23 g. of bromine and 4.52 g. sodium hydroxide in 160 ml. water) exactly as described for 2-acetyl-7-ethylfluorene in the preceding Example. The 7-butylfluorenone-2-carboxylic acid thus isolated had m.p. > 300° and was homogeneous by thin layer chromatography.

EXAMPLE 16

Dipotassium anthraquinone-2,6-dicarboxylate

Anthraquinone-2,6-dicarboxylic acid (1.00g) was dissolved in the minimum quantity of water (20 ml) containing one equivalent of potassium bicarbonate (0.68g) at the boil. The solution was filtered whilst hot and allowed to crystallise. The product which separated was filtered off, dried at 100°C, and analysed for the dihydrate. Analysis: Required Carbon 47.06, Hydrogen 2.47%; Found Carbon 47.09, Hydrogen 2.48%.

EXAMPLE 17

N,N-Diethylfluorenone-2-carboxamide

A mixture of fluorenone-2-carbonyl chloride (2.4g) and diethylamine (1.5g) in dry benzene (50ml) was heated to reflux for 2 hours. The mixture was allowed to cool and the solid was filtered, washed with benzene, then with water and dried in vacuo. Recrystallisation from ethanol gave N,N-diethylfluorenone-2-carboxamide, m.p. 90°–92°.

EXAMPLE 18

Dibutyl fluorenone-2,7-dicarboxylate

A suspension of fluorenone-2,7-dicarboxylic acid (6.0g) in dry n-butanol (200ml) with sulphuric acid (2ml) was stirred and heated to reflux. After 4 hours all the solid had dissolved and refluxing was continued for another 2 hours and the solution then allowed to cool. The crystalline product was removed by filtration, washed with n-butanol, then washed well with water and dried in vacuo to give pure dibutyl fluorenone-2,7-dicarboxylate m.p.: 99.5°–100.5°.

EXAMPLE 19

7-Butoxycarbonyl fluorenone-2-carboxylic acid sodium salt

Dibutyl fluorenone-2,7-dicarboxylate (3.8g) was added to a stirred refluxing solution of sodium hydroxide (400mg.) in dry n-butanol (75ml.). Stirring and refluxing were continued for 10 minutes and the mixture was allowed to cool. The crystalline product was filtered, washed with n-butanol and dried in vacuo. The solid was ground with water (10ml.) and the paste was filtered; this process was repeated and the solid washed with a little ice-cold water and dried to give pure 7-butoxycarbonyl fluorenone-2-carboxylic acid sodium salt monohydrate, m.p. >300°.

EXAMPLE 20

7-Butoxycarbonyl fluorenone-2-carboxylic acid

A portion (1.2g.) of the sodium salt of Example 29 was dissolved in warm water (40ml.), and the solution was quickly cooled to 20° and treated with 2N-hydrochloric acid (2ml.). The precipitated solid was filtered, washed well with water and dried in vacuo to give 7-butoxycarbonyl fluorenone-2-carboxylic acid, m.p. 248°–250°.

EXAMPLE 21–23

In the manner described in Examples 18, 19 and 20, were prepared the corresponding n-propyl esters:
Example 21: Dipropyl fluorenone-2,7-dicarboxylate, m.p. 146.5°–148°.
Example 22: 7-Propoxycarbonyl fluorenone-2-carboxylic acid sodium salt monohydrate, m.p. > 300°.
Example 23 7-Propoxycarbonyl fluorenone-2-carboxylic acid, m.p. 250°–252°.

EXAMPLE 24

Dihexylfuorenone-2,7-dicarboxylate

A suspension of fluorenone-2,7-dicarboxylic acid (5.0g) in n-hexanol (200 ml.) containing sulphuric acid (2 ml) was heated to reflux for 18 hours. The resulting dark solution was washed with water (5 × 75 ml) and the solid which separated during this washing was filtered, washed with a little n-hexanol and dried in vacuo. This product was dihexyl fluorenone-2,7-dicarboxylate, m.p. 89°–90°C; a further quantity was obtained by evaporating the mother-liquor to low volume under reduced pressure and allowing it to crystallise at 0°C.

EXAMPLE 25

7-Hexyloxyfluorenone-2-carboxylic acid sodium salt

Dihexyl fluorenone-2,7-dicarboxylate (2.18g) was added to a hot solution of sodium hydroxide (200 mg) in n-hexanol (35 ml) and the mixture was stirred and refluxed for 5 minutes and then allowed to cool, to 0°C. The resulting solid was removed by filtration, washed with a little n-hexanol, dried in vacuo and then ground with water (10ml). The resulting paste was filtered and the yellow solid was washed with a little water and dried in vacuo to give 7-hexyloxycarbonylfluorenone-2-carboxylic acid sodium salt monohydrate m.p. above 300°.

EXAMPLE 26

Fluorenone-2,7-dicarboxylic acid bis-ethanolamine salt

Fluorenone-2,7-dicarboxylic acid (2.68 g.) was suspended in water (10 mls) and treated with ethanolamine (1.22 g.). The mixture was warmed and stirred until all the solid had dissolved. The solution was treated with ethanol (100 mls), cooled and filtered to remove a small amount of solid. The filtrate was evaporated under reduced pressure. The residue was dissolved in water (2 to 3 mls) and treated with ethanol (100 mls). The solution was cooled to 0°C for 1 hour. The resulting yellow crystalline solid was filtered, washed with alcohol and dried in vacuo to give Fluorenone-2,7-dicarboxylic acid bis-ethanolamine salt which decomposed slowly above 145°C.

EXAMPLE 27

Anthraquinone-2,6-dicarboxylic acid bis-ethanolamine salt

Anthraquinone-2,6-dicarboxylic acid (2.96 g.) was suspended in methanol (50 mls.). Ethanolamine (1.36 g.) was added and the mixture boiled for 30 minutes. On cooling the pale yellow solid was filtered off, washed with methanol, dried at room temperature in vacuo, and analysed for the bis-ethanolamine salt.

Analysis: Required (for $C_{20}H_{22}N_2O_8$): Carbon 57.41; Hydrogen 5.30; and Nitrogen 6.70. Found: Carbon 57.48; Hydrogen 5.33; and Nitrogen 6.70.

EXAMPLE 28

Preparation of 7-Propoxycarbonylfluorenone-2-carboxamide

7-Propoxycarbonylfluorenone-2-carboxylic acid of Example 23 (4 g.) was treated with thionyl chloride (40 ml.); the mixture was heated under reflux for 2 hours; and the resulting solution was evaporated under reduced pressure to give yellow, crystalline, 7-propoxycarbonylfluorenone-2-carbonyl chloride. A portion of this acid chloride (2.1 g.) was stirred at room temperature for 1½ hours with 2N aqueous ammonia (30 ml.). The resulting solid was filtered, washed with water, dried and recrystallised from dimethylformamide to give 7-propoxycarbonylfluorenone-2-carboxamide, m.pt. 278°–279°C.

EXAMPLE 29

Preparation of 7-carbamoylfluorenone-2-carboxylic acid sodium salt

7-Propoxycarbonylfluorenone-2-carboxamide of Example 28 (1.46 g.) was added to a solution of sodium hydroxide (190 mg.) in refluxing propan-1-ol and the mixture heated under reflux, with stirring for 2 hours. The mixture was then cooled and the solid filtered, washed with a little propanol, dried under reduced pressure and then dissolved in warm water (ca. 20 ml.). The solution was filtered, the filtrate evaporated under reduced pressure, and the resulting solid recrystallised from water (ca. 5 ml.) to give 7-carbamoylfluorenone-2-carboxylic acid sodium salt, m.pt > 300°C.

EXAMPLE 30

Preparation of N,N - Diethyl-7-propoxycarbonylfluorenone-2-carboxamide

7-Propoxycarbonylfluorenone-2-carbonyl chloride [(2.1 g.) prepared as in Example 28] was treated with diethylamine (1 g.) in dry benzene (30 ml.) and the mixture was refluxed for 30 minutes. The resulting solution was cooled, washed twice with water, dried over sodium sulpahte and evaporated to dryness. The crystalline residue, m.pt. 123°–124°C was recrystallised from ethanol to give pure N,N-diethyl-7-propoxycarbonylfluorenone-2-carboxamide, m.pt. 124°–125°C.

EXAMPLE 31

Preparation of N,N-Diethyl-7-carbamoylfluorenone-2-carboxylic acid sodium salt N,N-Diethyl-7-propoxycarbonylfluorenone-2-carboxamide of Example 30 (815 mg.) was added to a solution of sodium hydroxide (90 mg.) in refluxing propan-1-ol (15 ml.). The solid dissolved rapidly and the solution was allowed to cool over 30 minutes, with stirring. The solid which separated on cooling was filtered, washed with a little propanol and dried in vacuo to give N,N-diethyl-7-carbamoylfluorenone-2-carboxylic acid sodium salt m.pt. > 300°C.

EXAMPLE 32

Preparation of N,N-Diethyl-7-carbamoylfluorenone-2-carboxylic acid

N,N-Diethyl-7-carbamoylfluorenone-2-carboxylic acid sodium salt of Example 31 (190 mg.) was dissolved in water (10 ml.) and the solution acidified with 2N $HC_1$ (0.3 ml.) to precipitate N,N-diethyl-7-carbamoylfluorenone-2-carboxylic acid m.p. 247°–248°C.

EXAMPLE 33

Preparation of Fluorenone-2,5-dicarboxylic acid

Acetic anhydride (17.7 g.) was added to a stirred suspension of aluminium chloride (64 g.) in dichloroethane (100 ml.). The resulting solution was cooled to 0°C and treated dropwise with stirring, below 10°C, with a solution of 4-acetylfluorene (27.86 g.) in dichloroethane (100 ml.). The mixture was stirred at room temperature for 1 hour and then at 40°C for 3 hours, and finally cooled to 0°C and decomposed with 2N hydrochloric acid (200 ml.). The dichloroethane solution was separated and the aqueous portion was extracted with chloroform.

The combined organic solution was washed with water and with aqueous sodium bicarbonate, dried over sodium sulphate and evaporated under reduced pressure. The residual solid was twice recrystallised from ethanol to give pure 2,5-diacetylfluorene, m.pt. 128°–129°C. A solution of sodium hydroxide (27.2 g.) in water (500 ml.) was cooled to 0°C, stirred, and treated dropwise with bromine (14.8 ml.). 2,5-Diacetylfluorene (5g.) was added, the temperature was raised to 60°C over 3 hours and kept at 60°C for 3 hours. The mixture was cooled and filtered and the filtrate was warmed to 60°C, treated with sodium acetate (230 g.) and then cooled to 0°C for 1 hour. The resulting yellow precipitate was dissolved in water (200 ml.) and the solution was acidified with concentrated hydrochloric acid. After heating on the stream bath for 1 hour the solid was filtered, washed with water and dried in vacuo to give fluorenone-2,5-dicarboxylic acid m.pt. 300°C.

EXAMPLE 34

Preparation of Fluorenone-2,6-dicarboxylic acid 2,6-Diacetylfluorene (m.p. 155°C) was prepared from 3-acetylfluorene and oxidised to fluorenone-2,6-dicarboxylic acid (m.p.>300°C) in the manner described in Example 33.

EXAMPLE 35

N,N-dibutyl-7-carbamoylfluorenone-2-carboxylic acid sodium salt

7-Propoxycarbonylfluorenone-2-carbonyl chloride (2.1g.) and dibutylamine (1.73g.) were refluxed in dry benzene (25 ml); the solid dissolved within 4 minutes and refluxing was continued for a total of 30 minutes. The solution was cooled, washed twice with water, dried over sodium sulphate and evaporated under reduced pressure. The resulting yellow gum was dissolved in propan-1-ol (15 ml) and the solution was added to a hot solution of sodium hydroxide (256 mg) in hot propan-1-ol (25 ml). The mixture was kept at 80°C. for 5 minutes and then evaporated to half volume and allowed to cool. The resulting yellow crystalline solid was filtered, washed with propanol, and dried to give pure N,N-dibutyl-7-carbamoylfluorenone-2-carboxylic acid sodium salt, m.p. > 300°C.

EXAMPLE 36

7-Propoxycarbonylfluorenone-2-carbonitrile

7-Propoxycarbonylfluorenone-2-carboxamide (318g.) was dissolved in warm dimethylformamide (50 ml.) and the solution was stirred and cooled to −25°C. Thionyl chloride (7.55 ml.) was added dropwise over 10 minutes to the stirred mixture which was then stirred at 0°C. for 3 hours and left to stand at 0°C. for 48 hours. The mixture was treated with ice water and the resulting yellow precipitate was filtered, washed with water and dried in vacuo to give pure 7-propoxycarbonylfluorenone-2-carbonitrile m.p. 198°–199°C.

EXAMPLE 37

7-(2-Butoxycarbonyl)fluorenone-2-carboxylic acid

A suspension of fluorenone-2,7-dicarboxylic acid (10g.) in butan-2-ol (300 ml.) containing sulphuric acid (3 ml.) was heated to reflux for 4 days. The yellow solution was cooled and the resulting yellow solid was filtered, washed well with butan-2-ol and dried to give pure di-2-butyl fluorenone-2-carboxylate m.p. 118°–119°C. This diester (3.04g.) was added in one portion to a hot solution of sodium hydroxide (320 mg.) in butan-2-ol (50 ml.) containing 1 drop of water. The mixture was stirred at reflux temperature for 10 minutes and then allowed to cool to room temperature. The resulting yellow solid was filtered, washed with butan-2-ol and then dissolved in water (15 ml.). The aquous solution was kept at 4°C. overnight, filtered to remove a small amount of solid, and carefully acidified with 2N hydrochloric acid. The yellow precipitate was filtered, washed with water and dried to give pure 7-(2-butoxycarbonyl)fluorenone-2-carboxylic acid m.p. 266°–267°C.

EXAMPLE 38

Dimethyl anthraquinone-2,6-dicarboxylate

Anthraquinone-2,6-dicarboxylic acid (1.0g.) was boiled under reflux with thionyl chloride (10 ml.) and dimethylformamide (0.1 ml.) for 45 minutes. The resulting clear solution was evaporated to dryness and methanol (20 ml.) was added. The suspension was boiled for 1 hour, cooled, and the yellow product filtered off and recrystallised from dimethylformamide, to give, after drying at 80°C. in vacuo, the diester, m.p. 260°C.

EXAMPLE 39

Anthraquinone-2,6-dicarboxamide

Anthraquinone-2,6-dicarboxylic acid (5.0 g.) was boiled with thionyl chloride (50 ml.) and dimethylformamide (0.25 ml.) for 45 min. The resulting clear solution was evaporated to dryness and the residual acid chloride treated with 0.880 ammonia. After standing for 30 minutes, the crude amide was filtered off, washed with water and dried, m.p. 420° (decomp.).

Example A - Aerosol Powder

| | |
|---|---|
| Disodium fluorenone-2,7-dicarboxylate (Micronised) | 2.0 g |
| Span 85 (Trade Name for Sorbitan Trioleate) | 40.0 mg |
| Saccharin Sodium (micronised) | 20.0 mg |
| Menthol | 20.0 mg |
| Arcton 11 (Trade Name) | 45.0 g |
| Arcton 12 (Trade Name) to | 100.0 ml |

The Disodium Carboxylate salt was micronised in a 3 inch Cox Fluid Energy Mill using an air pressure of about $7.10^5$ Newton/meter$^2$ at a feed rate of about 60 g of the salt per hour. In the resulting micronised powder, 93% by weight of the particles had a diameter not less than $2\mu$ and 98% by number of the particles had a diameter of not more than $7\mu$.

The Span 85 and Menthol were dissolved in Arcton 11 (Trade Name) and cooled to approximately 10°C. The micronised Disodium carboxylate salt and micronised Sodium saccharin were dispersed in the cooled solution and the resulting suspension was cooled to approximately −40°C. The Arcton 12, cooled to −40°C, was then added and the resulting suspension stirred with cooling.

The suspension was filled into suitable 10 ml aluminium containers each of which was closed with a 100$\mu$l metered dose valve.

The composition provides 2 $\mu$g of the Disodium carboxylate salt in each 100$\mu$l dose.

Example B - Nasal Drops.

| | |
|---|---|
| Disodium fluorenone-2,7-dicarboxylate | 0.5 g |
| Chlorbutol | 0.5 g |
| Sodium Chloride | 0.5 g |
| Distilled Water to | 100.0 ml |

The ingredients were dissolved together in Distilled Water (95 ml) at room temperature. The solution was made up to volume with the balance of the Distilled Water and clarified by passage through a filter of sintered glass, porosity No. 4.

Example C - Nasal Drops.

| | |
|---|---|
| Fluorenone-2,7-dicarboxylic acid (micronised powder) | 0.5 g |
| Hypromellose 50 | 0.6 g |
| Chlorbutol | 0.5 g |
| Sodium Chloride | 0.5 g |
| Distilled Water to | 100.0 ml |

Chlorbutol was dissolved in Distilled Water (30 ml) at 75°C. Hypromellose was added and dispersed. An ice-cold solution of sodium chloride in distilled Water (60 ml) was added, and the mixture stirred until Hypromellose dissolved completely. The fluorenone acid was added and thoroughly dispersed, and the mixture diluted to volume.

Example D - Eye Drops.

| | |
|---|---|
| Disodium fluorenone-2,7-dicarboxylate | 0.20 g |
| Sodium Chloride | 0.83 g |
| Methyl Hydroxybenzoate | 0.06 g |
| Propyl Hydroxybenzoate | 0.04 g |
| Distilled Water to | 100.00 ml |

Methyl and Propyl Hydroxybenzoate were dissolved in Distilled Water (70 ml) at 75°C. Sodium Chloride was added and dissolved and the solution allowed to cool. Disodium salt was added and dissolved, and the final solution made up to volume and sterilised by filtration.

Example E - Capsules of Powder

| | |
|---|---|
| Disodium fluorenone-2,7-dicarboxylate (0.5 to 7.0$\mu$ powder) | 4.0 mg |
| Lactose (30–90$\mu$ powder) | 46.0 mg |

The powders were mixed until homogenous and filled in suitable size hard gelatin capsules, 50 mg per capsule, for use in a powder inhalation device, such as the type described in U.K. Pat. No. 1,182,779.

Example F - Lotion for Topical Use.

| | |
|---|---|
| Disodium fluorenone-2,7-dicarboxylate | 1.5 g |
| Sorbitan Monolaurate | 0.6 g |
| Polysorbate 20 | 0.6 g |
| Cetostearyl Alcohol | 1.2 g |
| Glycerin | 6.0 g |
| Methyl Hydroxybenzoate to | 0.2 g |

To a solution of Methyl Hydroxybenzoate and Glycerin in Distilled Water (70 ml) at 75°C was added a mixture of Sorbitan Monolaurate, Polysorbate 20 and Cetostearyl Alcohol at the same temperature. The resulting emulsion was homogenised using high speed stirring and allowed to cool. A solution of the Disodium salt in the remaining Distilled Water was added and the whole stirred.

Example G - Injection Solution

| | |
|---|---|
| Disodium fluorenone-2,7-dicarboxylate | 10.0 mg |
| Water for Injection to | 1.0 ml |

The Disodium Salt was dissolved in half the Water for Injection. The remaining Distilled Water was added and the solution sterilised by filtration. The sterile solution was filled into an ampoule under aseptic conditions.

Example H - Aerosol Powder

| | |
|---|---|
| Disodium fluorenone-2,7-dicarboxylate | 400 mg |
| Sorbitan Trioleate | 200 mg |
| Trichlorofluoromethane | 4.5 g |
| Dichlorodifluoromethane to | 10.0 ml |

Sorbitan Trioleate was dissolved in Trichlorofluoromethane. Disodium salt was added and thoroughly dispersed. The mixture was transferred to a suitable aerosol canister and Dichlorodifluoromethane injected through the valve system. The composition provides 4 mg of Disodium salt in each 100$\mu$l dose.

| Example I - Aerosol Powder | |
|---|---|
| Fluorenone-2,7-dicarboxylic acid (0.5–7µ powder) | 500 mg |
| Sorbitan Trioleate | 100 mg |
| Saccharin (6–10µ powder) | 5 mg |
| Methanol | 2 mg |
| Sodium Sulphate (2–6µ powder) | 50 mg |
| Trichlorofluoromethane | 4.5 g |
| Dichlorodifluoromethane     to | 10.0 ml |

Sorbitan Trioleate and Methanol was dissolved in Trichlorofluoromethane. Acid, Saccharin and Sodium Sulphate were added and dispersed. The suspension was transferred to a suitable aerosol canister. Dichlorodifluoromethane was injected through the valve system. The composition provides 5 mg of Acid in each 100µl dose.

| Example J - Lozenge | |
|---|---|
| Disodium fluorenone-2,7-dicarboxylic acid | 50 mg |
| Mannitol | 400 mg |
| Dextrose Monohydrate | 400 mg |
| Magnesium Stearate | 20 mg |
| Granulated with a solution of Polyvinylpyrrolidone; 5% in 25% Alcohol. | |

A mixture of Disodium Salt, Mannitol and Dextrose Monohydrate was granulated with Polyvinylpyrrolidone in Alcohol, and the granule dried. Magnesium Stearate was sifted on and the mixture compressed to produce lozenges of the desired shape.

EXAMPLE K

Pharmaceutical Compositions

Pharmaceutical compositions of dimethylfluorenone-2,7-dicarboxylate were prepared from the same carrier ingredients and in similar manner to those described in Examples C and I.

EXAMPLE L

Pharmaceutical Compositions

Pharmaceutical compositions of anthraquinone-2,6-dicarboxylic acid were prepared from the same carrier ingredients and in similar manner to those described in Examples C and I.

What we claim is:

1. A method of preventing the symptoms of asthma or allergic rhinitis in a mammal having asthma or allergic rhinitis which comprises administering to said mammal a prophylactically effective amount of a compound of formula

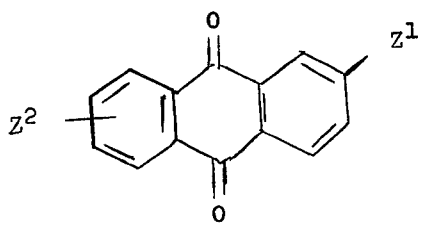

where $Z^1$ is selected from the group consisting of carboxyl, a pharmaceutically acceptable carboxylate salt and alkyl carboxylate wherein the alkyl moiety has 1 to 6 carbon atoms; and $Z^2$ is selected from the group consisting of hydrogen and a substituent $Z^1$ as defined herein.

2. A method of preventing the symptoms of asthma or allergic rhinitis in a mammal having asthma or allergic rhinitis which comprises administering to said mammal a prophylactically effective amount of a compound of the formula

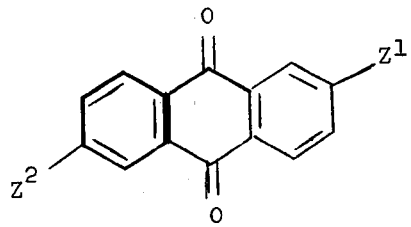

wherein $Z^1$ and $Z^2$ are the same or different and each is selected from the group consisting of carboxyl, pharmaceutically acceptable carboxylate salt, and alkyl carboxylate having 1 to 6 carbon atoms in the 'alkyl' moiety.

3. The method as claimed in claim 2 wherein $Z^1$ is selected from the group consisting of carboxyl and pharmaceutically acceptable carboxylate salt, and $Z^2$ is selected from $Z^1$ as defined herein.

4. The method as claimed in claim 3 wherein the carboxylate salt is selected from the group consisting of potassium, sodium, calcium, magnesium, ammonium and organic base salts selected from the group consisting of triethanolamine, diethylaminoethylamine, piperazine and morpholine.

5. The method according to claim 1 wherein the compound is administered by inhalation.

6. The method according to claim 5 wherein the compound is administered in the form of a powder having a particle size in the range from 0.5 to 7µ.

7. The method according to claim 1 wherein the amount of the compound is from 2 µg. to 100 mg. per Kg. bodyweight of said mammal.

8. The method according to claim 1 wherein the amount of the compound is from 20 µg to 0.2 mg. per kg. bodyweight of said mammal.

9. The method according to claim 1 wherein the asthma condition is extrinsic asthma.

10. The method according to claim 1 wherein the condition is allergic rhinitis.

11. The method of claim 1 wherein said compound is disodium anthraquinone-2,6-dicarboxylate.

* * * * *